(12) United States Patent
Levavi-Sivan et al.

(10) Patent No.: US 10,793,614 B2
(45) Date of Patent: *Oct. 6, 2020

(54) ANTAGONISTS OF FISH REPRODUCTION

(71) Applicant: Yissum Research Development Company of the Hebrew University of Jerusalem Ltd., Jerusalem (IL)

(72) Inventors: Berta Levavi-Sivan, Rosh Haayin (IL); Chaim Gilon, Jerusalem (IL)

(73) Assignee: Yissum Research Development Company of the Hebrew University ofJerusalem Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/175,012

(22) Filed: Oct. 30, 2018

(65) Prior Publication Data

US 2019/0169256 A1 Jun. 6, 2019

Related U.S. Application Data

(63) Continuation-in-part of application No. 15/326,602, filed as application No. PCT/IL2015/050739 on Jul. 16, 2015, now Pat. No. 10,155,790.

(60) Provisional application No. 62/025,618, filed on Jul. 17, 2014.

(51) Int. Cl.
| | |
|---|---|
| *C07K 7/22* | (2006.01) |
| *C07K 14/575* | (2006.01) |
| *A61K 9/00* | (2006.01) |
| *A23K 20/147* | (2016.01) |
| *A23K 50/80* | (2016.01) |
| *A23K 10/00* | (2016.01) |
| *A61K 38/00* | (2006.01) |

(52) U.S. Cl.
CPC ........ *C07K 14/57545* (2013.01); *A23K 10/00* (2016.05); *A23K 20/147* (2016.05); *A23K 50/80* (2016.05); *A61K 9/0029* (2013.01); *A61K 9/0053* (2013.01); *C07K 7/22* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,128,447 A | 7/1992 | Rovero | |
| 5,391,377 A | 2/1995 | Barnwell | |
| 10,155,790 B2 * | 12/2018 | Levavi-Sivan | ........ A23K 40/30 |

FOREIGN PATENT DOCUMENTS

| | | |
|---|---|---|
| WO | 2013/018097 A2 | 2/2013 |
| WO | 2014/089019 A1 | 6/2014 |

OTHER PUBLICATIONS

Aizen et al., (2007) Development of specific enzyme-linked immunosorbent assay for determining LH and FSH levels in tilapia, using recombinant gonadotropins. General and comparative endocrinology 153(1): 323-332.
Biran et al., (2008) Molecular identification and functional characterization of the kisspeptin/kisspeptin receptor system in lower vertebrates. Biology of reproduction 79(4): 776-786.
Biran et al., (2012) Neurokinin Bs and neurokinin B receptors in zebrafish-potential role in controlling fish reproduction. Proceedings of the National Academy of Sciences 109(26): 10269-10274.
Biran et al., (2014) Direct regulation of gonadotropin release by neurokinin B in tilapia (Oreochromis niloticus). Endocrinology 155(12): 4831-4842.
Drapeau et al., (1990) Antagonists for the neurokinin NK-3 receptor evaluated in selective receptor systems. Regulatory peptides 31(2): 125-135.
Evangelista et al., (1990) Analogs of neurokinin A (4-10) afford protection against gastroduodenal ulcers in rats. Peptides 11(2): 293-297.
Herbert et al., (1998) A large-scale process to produce microencapsulated proteins. Pharmaceutical research 15(2): 357-361.
Hurvitz, et al., (2005) Cloning of FSHβ, Lhβ, and glycoprotein a subunits from the Russian sturgeon (Acipenser gueldenstaedtii), β-subunit mRNA expression, gonad development, and steroid levels in immature fish. General and comparative endocrinology 140(1): 61-73.
Jacoby et al., (1986) Differentiation of multiple neurokinin receptors in the guinea pig ileum. Life Sci 39(21): 1995-2003.
Johnson et al., (1996) A month-long effect from a single injection of microencapsulated human growth hormone. Nature medicine 2(7): 795-799.
Levavi-Sivan et al., (2005) Cloning, characterization and expression of the D 2 dopamine receptor from the tilapia pituitary. Molecular and cellular endocrinology 236(1): 17-30.
Navarro (2012) New insights into the control of pulsatile GnRH release: the role of Kiss1/neurokinin B neurons. Frontiers in endocrinology 3: 489 ; pages.
O'Harte et al., (1991) Ranakinin: a novel NK1 tachykinin receptor agonist isolated with neurokinin B from the brain of the frog Rana ridibunda. Journal of neurochemistry 57(6): 2086-2091.
Pillai et al., (2001) Polymers in drug delivery. Current opinion in chemical biology 5(4): 447-451.
Sarang et al., (2005) Effect of piscine GH/IGF-I on final oocyte maturation in vitro in Heteropneustes fossilis. Fish Physiol Biochem 31(2-3): 231-233.
Sarau et al., (1997) Nonpeptide tachykinin receptor antagonists: I. Pharmacological and pharmacokinetic characterization of SB 223412, a novel, potent and selective neurokinin-3 receptor antagonist. Journal of Pharmacology and Experimental Therapeutics 281(3): 1303-1311.

(Continued)

*Primary Examiner* — Ronald T Niebauer
(74) *Attorney, Agent, or Firm* — J.A. Lindeman & Co., PLLC

(57) ABSTRACT

Peptide-based neurokinin antagonists of fish reproduction are disclosed. Compositions comprising antagonists of fish neurokinin and methods of inhibiting or delaying puberty, fish maturation or reproduction processes using these compounds are also provided.

20 Claims, 12 Drawing Sheets

Specification includes a Sequence Listing.

(56) References Cited

OTHER PUBLICATIONS

Sarau et al., (2000) Nonpeptide tachykinin receptor antagonists. II. Pharmacological and pharmacokinetic profile of SB-222200, a central nervous system penetrant, potent and selective NK-3 receptor antagonist. Journal of Pharmacology and Experimental Therapeutics 295(1): 373-381.

Tracy (1998) Development and Scale-up of a Microsphere Protein Delivery System_ Biotechnology progress 14(1): 108-115.

Zmora et al., (2017) Neurokinin B regulates reproduction via inhibition of kisspeptin in a teleost, the striped bass. J Endocrinol 233(2): 159-174.

* cited by examiner

SEQUENCE LISTING

```
<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION with Succinyl
<220> FEATURE:
<221> NAME/KEY: MOD_RES
<222> LOCATION: (4)..(4)
<223> OTHER INFORMATION: MeVal
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (7)..(7)
<223> OTHER INFORMATION: AMIDATION

<400> SEQUENCE: 1

Asp Ile Phe Xaa Xaa Leu Met
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: ACETYLATION with Succinyl
<220> FEATURE:
<221> NAME/KEY: MOD_RES
<222> LOCATION: (3)..(3)
<223> OTHER INFORMATION: MeVal
<220> FEATURE:
<221> NAME/KEY: MOD_RES
<222> LOCATION: (4)..(4)
<223> OTHER INFORMATION: bAla
<220> FEATURE:
<221> NAME/KEY: MOD_RES
<222> LOCATION: (6)..(6)
<223> OTHER INFORMATION: AMIDATION

<400> SEQUENCE: 2

Asp Phe Xaa Xaa Leu Met
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION with Succinyl
<220> FEATURE:
<221> NAME/KEY: MOD_RES
<222> LOCATION: (4)..(4)
<223> OTHER INFORMATION: MeVal
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (7)..(7)
<223> OTHER INFORMATION: AMIDATION

<400> SEQUENCE: 3

Asp Ser Phe Xaa Xaa Leu Met
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION with Succinyl
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: MeVal
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (7)..(7)
<223> OTHER INFORMATION: AMIDATION

<400> SEQUENCE: 4
```

```
Asp Ile Trp Xaa Xaa Leu Met
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION with Succinyl
<220> FEATURE:
<221> NAME/KEY: MOD_RES
<222> LOCATION: (2)..(2)
<223> OTHER INFORMATION: D-Trp
<220> FEATURE:
<221> NAME/KEY: MOD_RES
<222> LOCATION: (3)..(3)
<223> OTHER INFORMATION: MeVal
<220> FEATURE:
<221> NAME/KEY: MOD_RES
<222> LOCATION: (4)..(4)
<223> OTHER INFORMATION: bAla
<220> FEATURE:
<221> NAME/KEY: MOD_RES
<222> LOCATION: (6)..(6)
<223> OTHER INFORMATION: AMIDATION

<400> SEQUENCE: 5

Asp Trp Xaa Xaa Leu Met
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION with Succinyl
<220> FEATURE:
<221> NAME/KEY: MOD_RES
<222> LOCATION: (3)..(3)
<223> OTHER INFORMATION: D-Trp
<220> FEATURE:
<221> NAME/KEY: MOD_RES
<222> LOCATION: (4)..(4)
<223> OTHER INFORMATION: MeVal
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (7)..(7)
<223> OTHER INFORMATION: AMIDATION

<400> SEQUENCE: 6

Asp Ser Trp Xaa Xaa Leu Met
1               5

<210> SEQ ID NO 7
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
```

```
<223> OTHER INFORMATION: MeVal
<220> FEATURE:
<221> NAME/KEY: MOD_RES
<222> LOCATION: (2)..(2)
<223> OTHER INFORMATION: bAla

<400> SEQUENCE: 7

Xaa Xaa Leu Met
1
```

ANTAGONISTS OF FISH REPRODUCTION

SEQUENCE LISTING

The Sequence Listing submitted in text format (.txt) filed on Feb. 25, 2019, named "SequenceListing.txt", created on Feb. 25, 2019 (3.13 KB), is incorporated herein by reference.

FIELD OF THE INVENTION

The present invention is the field of fish reproduction and specifically related to peptidomimetics which are active as neurokinin B (NKB) and neurokinin F (NKF) antagonists and their use in inhibiting or delaying fish maturation of reproductive system.

BACKGROUND OF THE INVENTION

Reproductive function is tightly regulated by a complex network of central and peripheral factors, where the most important is GnRH. Recently, the neuropeptides kisspeptin (encoded by Kiss1) and neurokinin B (NKB, encoded by Tac3) have been placed as crucial at different stages of reproduction (Navarro V M. *Front Endocrinol.* 2012; 3:48.). Studies in humans have revealed that loss-of-function mutations in the genes encoding NKB or neurokinin 3 receptor (NK3R) lead to hypogonadotropic hypogonadism and infertility.

Neurokinin B (NKB) is a member of the tachykinin family of peptides. Inactivating mutations in the tachykinin 3 (tac3) or tac3 receptor (NKBR) gene are associated with pubertal failure and congenital hypogonadotrophic hypogonadism in humans. This suggests that NKB may have a critical role in human reproduction.

NKBs have direct action through receptors on the pituitary and indirect through receptors on gonadotropin-releasing-hormone (GnRH) neurons. NKBs bind to their cognate receptors, they stimulate their activity, which in turn provides an obligatory signal for gonadotropin secretion-thus gating down-stream events supporting reproduction. NKB is an important regulator of the hypothalamic-pituitary-gonadal axis and is the target of a range of regulators, such as steroid hormone feedback, nutritional and metabolic regulation.

Energy homeostasis and reproduction are the most important processes in an animal's life and are intimately related. Proper regulation of energy homeostasis and reproduction is fundamental for fitness and survival. Reproduction is an energy-intensive process, and precise interaction of regulators for energy balance and reproduction allows coordinated regulation of these two processes. In most fish species studied, seasonal variations in gonadal size are negatively correlated with serum growth hormone (GH) concentrations—e.g. when luteinizing hormone (LH) concentrations are high, due to gonadal size increase, GH concentrations are low, accompanied by very slow somatic growth.

Fish possess a large diversity of reproduction strategies, can be found in different environmental niches and use different timing regimes of sexual maturation. When compared with other vertebrates, fish have several unique characteristics. In contrast to tetrapod, where the cells in the pituitary are mixed, in fish there is a unique organization of specific calls in certain areas. Fish possesses a dual mode of gonadotrope regulation by GnRH, that combines both neuroglandular and neurovascular components. Moreover, different nerve terminals that secrete different neuropeptides innervate the pituitary. However, it is still unknown whether NKB or NKF neurons project to the pituitary in fish.

To date, a large number of tachykinins have been identified in a wide range of species from invertebrates to mammals. Tac1 encodes both substance P (SP) and NKA through alternative splicing. Tac2/Tac3 produces the peptide NKB, and Tac4 encodes hemokinin-1.

Three classes of mammalian tachykinin receptors (NK1, NK2, and NK3) have been identified, and these have preferential binding affinities for SP, NKA, and NKB, respectively. The mammalian TAC1 and TAC4 give rise to 2 active neuropeptides, whereas the TAC3 is the only TAC that give rise to only 1 neuropeptide, namely NKB.

Tachykinin (tac) and tac receptor genes were recently identified from many fish species (Biran 2012, PNAS 109: 10269-10274). Phylogenetic analysis showed that piscine Tac3s and mammalian neurokinin genes arise from one lineage. High identity was found among different fish species in the region encoding the NKB; all shared the common C-terminal sequence. Although the piscine Tac3 gene encodes for two putative tachykinin peptides, the mammalian orthologue encodes for only one. The second fish putative peptide, referred to as neurokinin F (NKF), is unique and found to be conserved among all tested fish species.

Zebrafish tac3a mRNA levels gradually increased during the first few weeks of life and peaked at pubescence. In the brain of zebrafish, tac3a and tac3b mRNA was observed in specific brain areas that are related to reproduction (Biran et al., 2008, Biol Reprod 79:776-786). Furthermore, a single ip injection of NKBa or NKF significantly increased LH levels in mature female zebrafish, and the tac3a and both tac3r genes were upregulated by estrogen (Biran et al., 2012, ibid), suggesting that the NKB/NKBR system may participate in neuroendocrine control of fish reproduction and that the role of the NKB system in the neuroendocrine control of reproduction is evolutionarily conserved in vertebrates.

Tilapia have become one of the most commercially important cultured freshwater fish, due to their high growth potential, short generation time, ease of spawning, and disease resistance.

It was shown (Biran et al., 2014, Endocrinology 155, 4831-42) that the recently identified neuropeptides denoted Neurokinin B (NKB) and Neurokinin F (NKF), that are secreted by the fish brain and involved in reproduction, can stimulate the release of follicle stimulating factor (FSH) and LH by direct (through activation of specific receptors at the pituitary level) or indirect (through the brain) mechanisms.

WO 2013/018097, to some of the inventor of the present invention, discloses NKB and NKF agonists for hormonal regulation in fish and specifically for advancing the onset of puberty, regulating the timing and amount of ovulation and spawning, synchronization or stimulation of reproduction, enhancing the development of gammets, enhancing vitellogenesis, induction of GnRH, induction of Kisspeptine, increase in the levels of hypothalamic neurohormones, increasing the level of LH or FSH and induction of oocyte maturation.

G. Drapeau et al., (Regul. Peptides, 31, 125, 1990) discloses the compound SR142801 (Trp$^7$, β-Ala$^8$-Neurokinin A, 4-10) as a potent antagonist of the tachykinin NK3 receptor in mammalians.

O'Harte, F. (J. Neurochem. 57 (6), 2086-2091, 1991) discloses the peptide analog denoted Ranakinin, an NK1 tachykinin receptor agonist isolated with neurokinin B from the brain of the frog Rana ridibunda.

Several small molecule, non-peptidic NKB antagonists are known in mammals, for example: SB-222200 (Sarau et al., 2000, J Pharmacol Exp Ther 295:373-381); Osanetant (SR-142,801) and talnetant (SB 223412) (Sarau et al., 1997, J Pharmacol Exp Ther 281:1303-1311).

While previous publications disclosed fish NKB peptide agonists for enhancing fertilization and shortening the time for maturation or mammalian NK-3 antagonists, none of the prior publications disclose NKB antagonists in fish. There is an unmet need for such antagonists for use in delaying maturation and controlling reproductive parameters in fish.

SUMMARY OF THE INVENTION

The present invention is based on the finding that inhibition of tac-3 receptor activity in fish by NKB antagonists can delay or inhibit maturation and reproduction. It was surprisingly found that alteration of specific amino acid residues in the sequence of NKB and NKF peptides result in change in their activity from agonistic to antagonistic toward maturation of fish reproductive system. Method for inhibiting fish maturation and for treating hormone-dependent problems or processes in fish, using NKB and NKF antagonists are also provided as well as use of NKB and NKF antagonists in pharmaceutical or food compositions. Peripherally active peptide-based NKB and NKF antagonists (herein denoted peptidomimetics) or other antagonists, that inhibit or eliminate the reproduction of fish can lead, among other processes, to increased growth rates and alteration in sex determination.

The present invention provides, according to one aspect a peptidomimetic according to Formula I:

$X_1$-NMeVal-$X_4$-Leu-Met-Z      (Formula I)

wherein:
the peptidomimetic consists of 5-10 amino acids;
$X_1$ is a stretch of 1-6 natural or non-natural amino acid residues and optionally an N-terminal capping moiety or modification;
NMeVal is an N-methyl-Valine residue or N-methyl-D-Valine residue;
$X_4$ is —NH(CH$_2$)$_n$—CO— wherein n is 2-6; and
Z represents the C-terminus of the peptide which may be amidated, acylated, reduced or esterified. Each possibility represents a separate embodiment of the present invention.

According to some embodiments $X_1$ comprises at least one aromatic amino acid residue in L or D configuration.

According to other embodiments, $X_1$ comprised a D-Trp residue.

According to some embodiments $X_1$ comprises at least one negatively charged (acidic) amino acid residue.

According to some embodiments, the C-terminus is amidated.

According to some embodiments, $X_1$ consists of 2 or 3 amino acids and a capped N-terminus. Each possibility represents a separate embodiment of the present invention.

According to some embodiments, $X_1$ consists of 2 or 3 amino acid residues comprising an aromatic residue, a negatively charged (acidic) residue and an N-terminus capping moiety. Each possibility represents a separate embodiment of the present invention.

According to some embodiments, the $X_1$ comprises a residue selected from an aliphatic amino acid residue and a polar, uncharged residue. Each possibility represents a separate embodiment of the present invention.

According to some embodiments, the aliphatic residue is selected from the group consisting of: Ala, Ile, Leu. Each possibility represents a separate embodiment of the present invention.

According to some embodiments, the polar, uncharged residue is selected from Ser and Thr. Each possibility represents a separate embodiment of the present invention.

According to some embodiments, $X_1$ comprises an aromatic residue selected from the group consisting of Phe, DPhe, Trp and DTrp; a negatively charged (acidic) residue selected from Glu and Asp; and a succinyl (Succ) N-terminus capping moiety. Each possibility represents a separate embodiment of the present invention.

According to yet other embodiments, $X_1$ comprises an aromatic residue selected from Phe, and DTrp; an Asp residue; a succinyl (Succ) N-terminus capping moiety, and optionally a residue selected from Ile and Ser. Each possibility represents a separate embodiment of the present invention.

According to some embodiments, the peptidomimetic is according to Formula II:

$X_1$-NMeVal-βAla-Leu-Met-NH$_2$      (Formula II)

wherein, $X_1$ is selected from the group consisting of: Succ-Asp-Phe; Succ-Asp-DPhe; Succ-Asp-Trp; Succ-Asp-DTrp; Succ-Asp-Ile-Phe; Succ-Asp-Ile-DPhe; Succ-Asp-Ile-Trp; Succ-Asp-Ile-DTrp; Succ-Asp-Ser-Phe; Succ-Asp-Ser-DPhe; Succ-Asp-Ser-Trp; Succ-Asp-Ser-DTrp, Succ-Glu-Phe; Succ-Glu-DPhe; Succ-Glu-Trp; Succ-Glu-DTrp; Succ-Glu-Ile-Phe; Succ-Glu-Ile-DPhe; Succ-Glu-Ile-Trp; Succ-Glu-Ile-DTrp; Succ-Glu-Ser-Phe; Succ-Glu-Ser-DPhe; Succ-Glu-Ser-Trp; and Succ-Glu-Ser-DTrp. Each possibility represents a separate embodiment of the present invention.

According to some embodiments, a peptidomimetic is provided consisting of 5-10 amino acid residues comprising a sequence set forth in SEQ ID NO: 7:

```
                                          (SEQ ID NO: 7)
                    NMeVal-βAla-Leu-Met.
```

According to some embodiment the peptidomimetic comprises a sequence of SEQ ID NO: 7, at least one aromatic amino acid residue and at least one negatively charged amino acid residue.

According to some embodiments, the peptidomimetic comprises a sequence of SEQ ID NO: 7, at least one aromatic amino acid residue, at least one negatively charged amino acid residue and at least one residue selected from an aliphatic amino acid residue and a polar, uncharged residue. Each possibility represents a separate embodiment of the present invention.

According to some embodiments, the peptidomimetic comprises a capped N-terminus.

According to some embodiments the peptidomimetic comprises an amidated C-terminus.

According to some embodiments the peptidomimetic consist of 5, 6, 7, 8, 9 or amino acid residues and an optional N-terminal capping group. Each possibility represents a separate embodiment of the present invention.

According to some embodiments, the peptidomimetic consists of 5-10 amino acid residues, an amidated C-terminus and an N-terminal capping moiety. Each possibility represents a separate embodiment of the present invention.

According to some embodiments, the peptidomimetic consists of 6-7 amino acid residues comprising the sequence of SEQ ID NO: 7, and a sequence selected from the group consisting of: Succ-Asp-Phe; Succ-Asp-DPhe; Succ-Asp- Trp; Succ-Asp-DTrp; Succ-Asp-Ile-Phe; Succ-Asp-Ile-DPhe; Succ-Asp-Ile-Trp; Succ-Asp-Ile-DTrp; Succ-Asp-Ser-Phe; Succ-Asp-Ser-DPhe; Succ-Asp-Ser-Trp; Succ-Asp-Ser-DTrp, Succ-Glu-Phe; Succ-Glu-DPhe; Succ-Glu-Trp; Succ-Glu-DTrp; Succ-Glu-Ile-Phe; Succ-Glu-Ile-DPhe; Succ-Glu-Ile-Trp; Succ-Glu-Ile-DTrp; Succ-Glu-Ser-Phe; Succ-Glu-Ser-DPhe; Succ-Glu-Ser-Trp; and Succ-Glu-Ser-DTrp.

According to some embodiments the at least one N-terminal capping moiety is a dicarboxylic acid residue. According to some embodiments the at least one N-terminal capping moiety is selected from the group consisting of: succinyl, oxalyl, malonyl, glutaryl, adipoyl, pimaloyl, suberoyl, and acetyl. Each possibility represents a separate embodiment of the present invention.

According to some specific embodiments the peptidomimetic is selected from the group consisting of:

```
(SEQ ID NO: 1, Ant-1)
Succ-Asp-Ile-Phe-N(Me)Val-βAla-Leu-Met-NH2;

(SEQ ID NO: 2, Ant-2)
Succ-Asp-Phe-N(Me)Val-βAla-Leu-Met-NH2;

(SEQ ID NO: 3, Ant-3)
Succ-Asp-Ser-Phe-N(Me)Val-βAla-Leu-Met-NH2;

(SEQ ID NO: 4, Ant-4)
Succ-Asp-Ile-D-Trp-N(Me)Val-βAla-Leu-Met-NH2;

(SEQ ID NO: 5, Ant-5)
Succ-Asp-D-Trp-N(Me)Val-βAla-Leu-Met-NH2;
and (SEQ ID NO: 6, Ant-6)
Succ-Asp-Ser-D-Trp-N(Me)Val-βAla-Leu-Met-NH2;
``` wherein Succ denotes a succinyl.

It is to be explicitly understood that previously known peptides are excluded from the present invention.

According to some embodiments, the peptidomimetic further comprises a permeability-enhancing moiety. Any moiety known in the art to facilitate actively or passively or enhance permeability of the compound into cells may be used in the peptidomimetics according to the present invention. The permeability-enhancing moiety may be connected to any position in the peptide moiety, directly or through a spacer or linker.

The present invention provides, according to another aspect, a composition comprising a peptidomimetic of formula I.

According to some embodiments, the composition comprising a peptidomimetic according to Formula I is selected from a pharmaceutical composition and a food composition.

According to some embodiments the composition comprises a peptidomimetic according to Formula I wherein $X_1$ comprises at least one aromatic amino acid residue in L or D configuration.

According to some embodiments the composition comprises a peptidomimetic according to Formula I wherein $X_1$ comprised a D-Trp residue.

According to some embodiments the composition comprises a peptidomimetic according to Formula I wherein $X_1$ comprises at least one negatively charged (acidic) amino acid residue.

According to some embodiments the composition comprises a peptidomimetic according to Formula I wherein the C-terminus is amidated.

According to some embodiments the composition comprises a peptidomimetic according to Formula I wherein $X_1$ consists of 2 or 3 amino acids and a capped N-terminus. Each possibility represents a separate embodiment of the present invention.

According to some embodiments the composition comprises a peptidomimetic according to Formula I wherein $X_1$ consists of 2 or 3 amino acid residues comprising an aromatic residue, a negatively charged (acidic) residue, an amidated C-terminus and an N-terminus capping moiety. Each possibility represents a separate embodiment of the present invention.

According to some embodiments the composition comprises a peptidomimetic according to Formula I wherein $X_1$ comprises a residue selected from an aliphatic amino acid residue and a polar, uncharged residue. Each possibility represents a separate embodiment of the present invention.

According to some embodiments the composition comprises a peptidomimetic according to Formula I wherein the aliphatic residue is selected from the group consisting of: Ala, Ile, and Leu. Each possibility represents a separate embodiment of the present invention.

According to some embodiments the composition comprises a peptidomimetic according to Formula I wherein the polar, uncharged residue is selected from Ser and Thr. Each possibility represents a separate embodiment of the present invention.

According to some embodiments the composition comprises a peptidomimetic according to Formula I wherein $X_1$ comprises an aromatic residue selected from the group consisting of Phe, DPhe, Trp and DTrp; a negatively charged (acidic) residue selected from Glu and Asp; and a succinyl (Succ) N-terminus capping moiety. Each possibility represents a separate embodiment of the present invention.

According to some embodiments the composition comprises a peptidomimetic according to Formula I wherein $X_1$ comprises an aromatic residue selected from Phe, and DTrp; an Asp residue; a succinyl (Succ) N-terminus capping moiety, and optionally a residue selected from Ile and Ser. Each possibility represents a separate embodiment of the present invention.

According to some embodiments, the composition comprises a peptidomimetic according to formula II:

$$X_1\text{-NMeVal-}\beta\text{Ala-Leu-Met-NH}_2 \quad \text{(Formula II)};$$

wherein, $X_1$ is selected from the group consisting of: Succ-Asp-Phe; Succ-Asp-DPhe; Succ-Asp-Trp; Succ-Asp-DTrp; Succ-Asp-Ile-Phe; Succ-Asp-Ile-DPhe; Succ-Asp-Ile-Trp; Succ-Asp-Ile-DTrp; Succ-Asp-Ser-Phe; Succ-Asp-Ser-DPhe; Succ-Asp-Ser-Trp; Succ-Asp-Ser-DTrp, Succ-Glu-Phe; Succ-Glu-DPhe; Succ-Glu-Trp; Succ-Glu-DTrp; Succ-Glu-Ile-Phe; Succ-Glu-Ile-DPhe; Succ-Glu-Ile-Trp; Succ-Glu-Ile-DTrp; Succ-Glu-Ser-Phe; Succ-Glu-Ser-DPhe; Succ-Glu-Ser-Trp; and Succ-Glu-Ser-DTrp. Each possibility represents a separate embodiment of the present invention.

According to some embodiments the composition comprises a peptidomimetic consisting of 5-10 amino acid residues comprising the sequence NMeVal-βAla-Leu-Met (SEQ ID NO: 7).

According to some embodiment the composition comprises a peptidomimetic comprising a sequence of SEQ ID NO: 7, at least one aromatic amino acid residue and at least one negatively charged amino acid residue.

According to some embodiments, the composition comprises a peptidomimetic comprising a sequence of SEQ ID NO: 7, at least one aromatic amino acid residue, at least one negatively charged amino acid residue and at least one residue selected from an aliphatic amino acid residue and a polar, uncharged residue. Each possibility represents a separate embodiment of the present invention.

According to some embodiments, the composition comprises a peptidomimetic comprising a capped N-terminus.

According to some embodiments the composition comprises a peptidomimetic comprising an amidated C-terminus.

According to some embodiments the composition comprises a peptidomimetic consisting of 5, 6, 7, 8, 9 or 10 amino acid residues and an optional N-terminal capping group. Each possibility represents a separate embodiment of the present invention.

According to some embodiments, the composition comprises a peptidomimetic consisting of 5-10 amino acid residues, an amidated C-terminus and an N-terminal capping moiety. Each possibility represents a separate embodiment of the present invention.

According to some embodiments, the composition comprises a peptidomimetic consisting of 6-7 amino acid residues comprising the sequence of SEQ ID NO: 7, and a sequence selected from the group consisting of: Succ-Asp-Phe; Succ-Asp-DPhe; Succ-Asp-Trp; Succ-Asp-DTrp; Succ-Asp-Ile-Phe; Succ-Asp-Ile-DPhe; Succ-Asp-Ile-Trp; Succ-Asp-Ile-DTrp; Succ-Asp-Ser-Phe; Succ-Asp-Ser-DPhe; Succ-Asp-Ser-Trp; Succ-Asp-Ser-DTrp, Succ-Glu-Phe; Succ-Glu-DPhe; Succ-Glu-Trp; Succ-Glu-DTrp; Succ-Glu-Ile-Phe; Succ-Glu-Ile-DPhe; Succ-Glu-Ile-Trp; Succ-Glu-Ile-DTrp; Succ-Glu-Ser-Phe; Succ-Glu-Ser-DPhe; Succ-Glu-Ser-Trp; and Succ-Glu-Ser-DTrp.

According to some embodiments the at least one N-terminal capping moiety is selected from the group consisting of: succinyl, oxalyl, malonyl, glutaryl, adipoyl, pimaloyl, suberoyl, acetyl, and other dicarboxylic acid residues. Each possibility represents a separate embodiment of the present invention.

According to some specific embodiments the composition comprises a peptidomimetic selected from the group consisting of:

```
(SEQ ID NO: 1, Ant-1)
Succ-Asp-Ile-Phe-N(Me)Val-βAla-Leu-Met-NH₂;

(SEQ ID NO: 2, Ant-2)
Succ-Asp-Phe-N(Me)Val-βAla-Leu-Met-NH₂;

(SEQ ID NO: 3, Ant-3)
Succ-Asp-Ser-Phe-N(Me)Val-βAla-Leu-Met-NH₂;

(SEQ ID NO: 4, Ant-4)
Succ-Asp-Ile-D-Trp-N(Me)Val-βAla-Leu-Met-NH₂;

(SEQ ID NO: 5, Ant-5)
Succ-Asp-D-Trp-N(Me)Val-βAla-Leu-Met-NH₂;
and (SEQ ID NO: 6, Ant-6)
Succ-Asp-Ser-D-Trp-N(Me)Val-βAla-Leu-Met-NH₂;
``` wherein Succ denotes a succinyl.
Each possibility represents a separate embodiment of the present invention.

A pharmaceutical composition according to the invention comprises an NKB or NKF antagonist peptidomimetic as defined above and an optional acceptable carrier, diluent, salt or excipient.

A food composition according to the present invention comprises an NKB antagonist peptidomimetic as defined above and an optional food additive. Any food additive known in the art may be used in a food composition according to the invention. This includes but is not limited to color additives, taste additives etc. Nutrients, including but not limited to proteins, carbohydrates, fats minerals, vitamins etc., may be also included in the food compositions of the present invention. A food composition according to the invention may comprise nutrients and food additives in addition to at least one active NKB or NKF antagonist.

According to some embodiments, the food composition comprises food pellets which are coated with at least one NKB or NKF antagonist.

A pharmaceutical or food composition as defined above, for use as an NKB antagonist is also within the scope of the present invention.

A composition comprising a peptidomimetic according to the invention may be administered to fish by any manner or route known in the art including parenteral administration and enteral administration. According to some embodiments, parenteral administration includes but is not limited to any type of injection. According to some embodiments, enteral administration includes but is not limited to oral administration, including administration as additive to the food, administration by immersion, including administration as additive to the drinking water, and intragastric administration via gavage.

According to some embodiments the composition is administered to fish as part of regular food or water consumption.

According to some embodiments, the composition is administered to fish in a volume of water to be taken up by the gills.

The invention also provides according to another aspect a composition comprising an NKB antagonist for use in inhibiting at least one parameter of fish reproduction or maturation.

An NKB antagonist according to the invention is a compound capable of binding to a piscine tachykinin 3 (tac3) receptor and inhibiting its activity. NKF antagonists are also within the definition of NKB antagonists.

According to some embodiments, the composition for use in inhibiting at least one parameter of fish reproduction or maturation comprises a peptidomimetic selected from the group consisting of: a peptidomimetic of Formula I, as defined above; a peptidomimetic of Formula II, as defined above; and a peptidomimetic of 5-10 amino acid residues comprising the sequence of SEQ ID NO: 7.

According to some embodiments, the composition for use in inhibiting at least one parameter of fish reproduction or maturation comprises a peptidomimetic selected from the group consisting of:

```
(SEQ ID NO: 1, Ant-1)
Succ-Asp-Ile-Phe-N(Me)Val-βAla-Leu-Met-NH₂;

(SEQ ID NO: 2, Ant-2)
Succ-Asp-Phe-N(Me)Val-βAla-Leu-Met-NH₂;

(SEQ ID NO: 3, Ant-3)
Succ-Asp-Ser-Phe-N(Me)Val-βAla-Leu-Met-NH₂;

(SEQ ID NO: 4, Ant-4)
Succ-Asp-Ile-D-Trp-N(Me)Val-βAla-Leu-Met-NH₂;

(SEQ ID NO: 5, Ant-5)
Succ-Asp-D-Trp-N(Me)Val-βAla-Leu-Met-NH₂;
and (SEQ ID NO: 6, Ant-6)
Succ-Asp-Ser-D-Trp-N(Me)Val-βAla-Leu-Met-NH₂;
``` wherein Succ denotes a succinyl. Each possibility represents a separate embodiment of the present invention.

According to other embodiments, the composition for use in inhibiting at least one parameter of fish reproduction or maturation comprises a non-peptidic NKB antagonist.

According to some specific embodiments, the composition for use in inhibiting at least one parameter of fish reproduction or maturation comprises a non-peptidic NKB antagonist selected from the group consisting of: (S)-(2)-N-(a-ethylbenzyl)-3-methyl-2-phenylquinoline-4-carboxamide (also denoted SB-222200); (S)-(1)-N-{{3-[1-benzoyl-3-(3,4-dichlorophenyl)piperidin-3-yl]prop-1-yl}-4-phenylpiperidin-4-yl}-N-methyl acetamide (also denoted Osanetant and SR-142,801), and (S)-(2)-N-(a-ethylbenzyl)-3-hydroxy-2-phenylquinoline-4-carboxamide (also denoted talnetant and SB 223412). Each possibility represents a separate embodiment of the present invention.

The present invention provides according to yet another aspect, a method of inhibiting at least one parameter of fish reproduction or maturation, the method comprising administering to fish a composition comprising an NKB antagonist.

According to some embodiments, the composition is selected from the group consisting of a pharmaceutical composition and a food composition.

Any NKB antagonist compound capable of binding to a piscine tac3 receptor and inhibiting its activity may be used according to this aspect.

According to some embodiments, the method comprises administering to fish a composition comprising a peptidomimetic selected from the group consisting of: a peptidomimetic of Formula I, as defined above; a peptidomimetic of Formula II, as defined above; and a peptidomimetic of 5-10 amino acid residues comprising the sequence of SEQ ID NO: 7.

According to some embodiments, the composition comprises a peptidomimetic selected from the group consisting of:

```
(SEQ ID NO: 1, Ant-1)
Succ-Asp-Ile-Phe-N(Me)Val-βAla-Leu-Met-NH₂;

(SEQ ID NO: 2, Ant-2)
Succ-Asp-Phe-N(Me)Val-βAla-Leu-Met-NH₂;

(SEQ ID NO: 3, Ant-3)
Succ-Asp-Ser-Phe-N(Me)Val-βAla-Leu-Met-NH₂;

(SEQ ID NO: 4, Ant-4)
Succ-Asp-Ile-D-Trp-N(Me)Val-βAla-Leu-Met-NH₂;

(SEQ ID NO: 5, Ant-5)
Succ-Asp-D-Trp-N(Me)Val-βAla-Leu-Met-NH₂;
and (SEQ ID NO: 6, Ant-6)
Succ-Asp-Ser-D-Trp-N(Me)Val-βAla-Leu-Met-NH₂;
``` wherein Succ denotes a succinyl.
Each possibility represents a separate embodiment of the present invention.

According to other embodiments, the composition comprises a non-peptidic NKB antagonist.

According to some specific embodiments, the composition comprises a non-peptidic NKB antagonist selected from the group consisting of: (S)-(2)-N-(a-ethylbenzyl)-3-methyl-2-phenylquinoline-4-carboxamide (also denoted SB-222200); (S)-(1)-N-{{3-[1-benzoyl-3-(3,4-dichlorophenyl)piperidin-3-yl]prop-1-yl}-4-phenylpiperidin-4-yl}-N-methylacetamide (also denoted Osanetant and SR-142,801), and (S)-(2)-N-(a-ethylbenzyl)-3-hydroxy-2-phenylquinoline-4-carboxamide (also denoted talnetant and SB 223412). Each possibility represents a separate embodiment of the present invention.

A pharmaceutical composition according to the invention administered in a method of inhibiting at least one parameter of fish reproduction or maturation, comprises an NKB antagonist and an optional acceptable carrier, diluent, salt or excipient.

A food composition according to the present invention administered in a method of inhibiting at least one parameter of fish reproduction or maturation, comprises an NKB antagonist and an optional food additive. A food composition according to the invention may also include nutrients and food additives, including but not limited to proteins, carbohydrates, fats, minerals, vitamins etc., may be also included in the food compositions of the present invention.

Inhibition of at least one parameter of piscine reproduction or maturation includes but it not limited to: delaying or eliminating puberty in general or precocious puberty in particular; regulating sex (gender) determination and differentiation (the process of gonad development after sex has been determined) and spawning (discharge of eggs and sperm). Also included within the scope is treatment of hormone-dependent problems or processes in fish which are connected to reproduction.

According to some embodiments, inhibition of piscine reproduction or maturation results in increased weight of the treated fish.

Fish according to the invention include any type of fish from any class, subclass, order, family or genus including farmed fish, edible fish and ornamental fish. According to some non-limitative embodiments, the fish is selected from the group consisting of: tilapia, carp, salmon, bass, catfish and mullet.

Administration of the NKB antagonists to fish according to the methods of the present invention can be performed by any manner known in the art including but not limited to parenteral administration, oral administration and administration by immersion.

According to some embodiments the NKB antagonists are administered to fish as part of food or water consumption.

According to some embodiments, the compounds are administered to fish in a volume of water to be taken up by the gills.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 3A, the effect on luciferase activity, of the non-peptide antagonist alone as compared with hNKB, tilapia NKB or tilapia NKF. FIG. 3B, the effect on luciferase activity of different concentrations of the antagonist added concomitantly with 0.1 nM of the native ligands (NKB or NKF).

FIG. 4A, the effect of the non-peptide antagonist alone on the luciferase activity in comparison with hNKB, tilapia NKB or tilapia NKF, at 0.1 nM ($10^{-8}$ M. FIG. 4B, the effect of different concentrations of the antagonist added concomitantly with 0.1 nM of the native ligands (NKB or NKF).

FIG. 11 proliferating cell nuclear antigen (PCNA) expression levels in the testes of injected fish at day 27.

FIG. 12A fish growth rate (gr) with and without the antagonists. FIG. 12B representative photographs of the fish of FIG. 12A. The three fish on the left are the control fish, and the three fish on the right were fed with the antagonist Ant-6.

DETAILED DESCRIPTION OF THE INVENTION

Figure 1A:
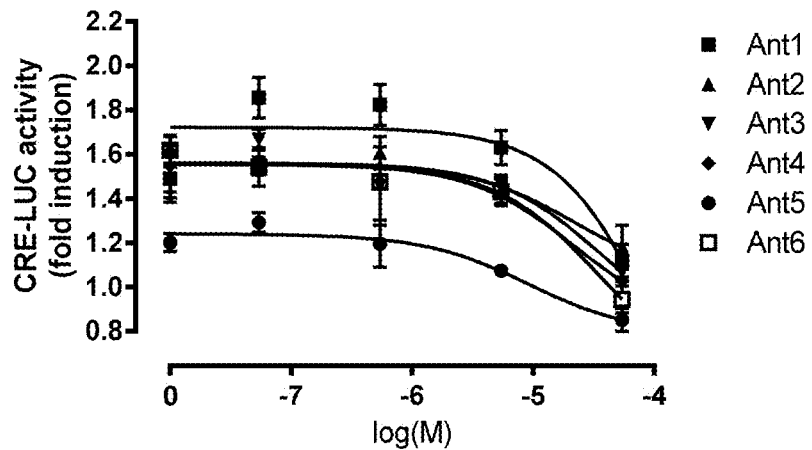
FIGS. 1A and 1B shows the effect of six peptidomimetics in inhibiting signal transduction (FIG. 1A CRE activation, FIG. 1B SRE activation) in tilapia. Each antagonist was added at different concentration concomitantly with NKB at $1*10^{-8}$ M (=0.1 nM). Tilapia NKB increased the luciferase activity by 1.8 fold and the reduction of the response by the various polypeptides is shown.

The present invention provides inhibitors of reproduction of fish and methods for controlling their maturation and growth. The invention is based on inhibition of tachykinin 3 receptor (tac-3 receptor) activity by peptide-based or small molecule antagonists of the tac-3 ligands NKB and NKF.

According to some embodiments of the present invention, the NKB antagonists are peptide-based compounds (peptidomimetics) according to the following formula:

$X_1$—$X_2$—$X_3$-NMeVal-$X_4$-Leu-Met-$NH_2$ wherein
  $X_1$ is any amino acid or non-natural amino acid mimetic or alternatively is null (no amino acid);
  $X_2$ is any amino acid or non-natural amino acid mimetics or alternatively is null (no amino acid);
  $X_3$ is any amino acid, preferably D aromatic amino acid, most preferably D-Trp or alternatively is null (no amino acid);
  $X_4$ is spacer of the type —NH$(CH_2)_n$—CO— where n=2-6, or alternatively spacer of the type -(Pro)$_n$- where n=1-6.

The present invention provides peptidomimetics of 5-10 amino acids and an optional N-terminal capping moiety, wherein the peptidomimetic is selected from the group consisting of:
  i. a compound of Formula I: $X_1$-NMeVal-$X_4$-Leu-Met-Z, wherein: $X_1$ is a stretch of 1-6 natural or non-natural amino acid residues; NMeVal is an N-methyl-Valine residue or N-methyl-D-Valine residue; $X_4$ is —NH$(CH_2)_n$—CO— wherein n is 2-6; and Z represents the C-terminus of the peptide which may be amidated, acylated, reduced or esterified;
  ii. a compound of formula II: $X_1$-NMeVal-$X_4$-Leu-Met-$NH_2$ wherein, $X_1$ is selected from the group consisting of: Succ-Asp-Phe; Succ-Asp-DPhe; Succ-Asp-Trp; Succ-Asp-DTrp; Succ-Asp-Ile-Phe; Succ-Asp-Ile-DPhe; Succ-Asp-Ile-Trp; Succ-Asp-Ile-DTrp; Succ-Asp-Ser-Phe; Succ-Asp-Ser-DPhe; Succ-Asp-Ser-Trp; Succ-Asp-Ser-DTrp, Succ-Glu-Phe; Succ-Glu-DPhe; Succ-Glu-Trp; Succ-Glu-DTrp; Succ-Glu-Ile-Phe; Succ-Glu-Ile-DPhe; Succ-Glu-Ile-Trp; Succ-Glu-Ile-DTrp; Succ-Glu-Ser-Phe; Succ-Glu-Ser-DPhe; Succ-Glu-Ser-Trp; and Succ-Glu-Ser-DTrp; and $X_4$ is βAla; and
  iii. a compound comprising the sequence NMeVal-βAla-Leu-Met (SEQ ID NO: 7).

Compositions comprising peptidomimetics according to the invention and methods for their use are also provided.

According to some specific embodiments, the composition of the invention comprises as an active ingredient a compound selected from the group consisting of: Ant-1 to Ant-6

```
(SEQ ID NO: 1, Ant-1)
Succ-Asp-Ile-Phe-N(Me)Val-βAla-Leu-Met-NH2;

(SEQ ID NO: 2, Ant-2)
Succ-Asp-Phe-N(Me)Val-βAla-Leu-Met-NH2;

(SEQ ID NO: 3, Ant-3)
Succ-Asp-Ser-Phe-N(Me)Val-βAla-Leu-Met-NH2;

(SEQ ID NO: 4, Ant-4)
Succ-Asp-Ile-D-Trp-N(Me)Val-βAla-Leu-Met-NH2;

(SEQ ID NO: 5, Ant-5)
Succ-Asp-D-Trp-N(Me)Val-βAla-Leu-Met-NH2;
and (SEQ ID NO: 6, Ant-6)
Succ-Asp-Ser-D-Trp-N(Me)Val-βAla-Leu-Met-NH2.
```

The peptides of the present invention are preferably synthesized using conventional synthesis techniques known in the art, e.g., by chemical synthesis techniques including peptidomimetic methodologies. These methods include exclusive solid phase synthesis, partial solid phase synthesis methods, fragment condensation, classical solution synthesis. Solid phase peptide synthesis procedures are well known in the art. A skilled artesian may synthesize any of the peptides of the present invention by using an automated peptide synthesizer using standard chemistry such as, for example, t-Boc or Fmoc chemistry. Synthetic peptides can be purified by preparative high performance liquid chromatography, and the composition of which can be confirmed via amino acid sequencing. Conjugation of peptidic and permeability moieties may be performed using any methods known in the art, either by solid phase or solution phase chemistry. Some of the preferred compounds of the present invention may conveniently be prepared using solution phase synthesis methods. Other methods known in the art to prepare compounds like those of the present invention can be used and are comprised in the scope of the present invention.

N-terminal capping or modification according to the present invention denotes alteration of the peptide's sequence by covalently attaching a chemical moiety to the terminal amine resulting in modified charge, activity and/or stability to cleavage by amino peptidases.

Non-limitative examples of a permeability-enhancing moiety include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides. According to some embodiments, the hydrophobic moiety is a lipid moiety or an amino acid moiety.

A permeability-enhancing moiety may be connected to any position in the peptide moiety, directly or through a spacer. According to specific embodiments, the cell-permeability moiety is connected to the amino terminus of the peptide moiety. The optional connective spacer may be of varied lengths and conformations comprising any suitable chemistry including but not limited to amine, amide, carbamate, thioether, oxyether, sulfonamide bond and the like. Non-limiting examples for such spacers include amino acids, sulfone amide derivatives, amino thiol derivatives and amino alcohol derivatives.

The term "peptide" or "peptide-based" as used herein is meant to encompass natural (genetically encoded), non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides and peptidomimetics of the present invention are preferably utilized in a linear form, although it will be appreciated that in cases where cyclization does not severely interfere with peptide characteristics, cyclic forms of the peptide can also be utilized.

The amino acids used in this invention are those which are available commercially or are available by routine synthetic methods. Certain residues may require special methods for incorporation into the peptide, and sequential, divergent or convergent synthetic approaches to the peptide sequence are useful in this invention. Natural coded amino acids and their derivatives are represented by three-letter codes according to IUPAC conventions. When there is no indication, either the L or D isomers may be used. When a "D"—precedes the amino acid, a D isomer is used.

Conservative substitution of amino acids as known to those skilled in the art are within the scope of the present invention. Conservative amino acid substitutions includes replacement of one amino acid with another having the same type of functional group or side chain e.g. aliphatic, aromatic, positively charged, negatively charged. These substitutions may enhance oral bioavailability, affinity to the target protein, metabolic stability, penetration into the central nervous system, targeting to specific cell populations and the like. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following is an example of classification of the amino acids into six groups, each contains amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), methionine (M), Valine (V); and
6) Phenylalanine (F), Tyrosine (Y), Tryptophan (W).

Other classifications into somehow different groups (for example, aliphatic, polar, non-polar, hydrophilic, hydrophopic etc.) are also known in the art and can be used for conservative amino acid substitutions according to the present invention.

Also included within the scope of the invention are salts of the peptides, analogs, and chemical derivatives of the peptides of the invention.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

A "chemical derivative" as used herein refers to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated.

"Functional derivatives" of the peptides of the invention as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

The term "peptide analog" indicates molecule which has the amino acid sequence according to the invention except for one or more amino acid changes or one or more modification/replacement of an amide bond. Peptide analogs include amino acid substitutions and/or additions with natural or non-natural amino acid residues, and chemical modifications which do not occur in nature. Peptide analogs include peptide mimetics. A peptide mimetic or "peptidomimetic" means that a peptide according to the invention is modified in such a way that it includes at least one non-coded residue or non-peptidic bond. Such modifications include, e.g., alkylation and more specific methylation of one or more residues, insertion of or replacement of natural amino acid by non-natural amino acids, replacement of an amide bond with other covalent bond. A peptidomimetic according to the present invention may optionally comprises at least one bond which is an amide-replacement bond such as urea bond, carbamate bond, sulfonamide bond, hydrazine bond, or any other covalent bond. The design of appropriate "analogs" may be computer assisted. Additional peptide analogs according to the present invention comprise a specific peptide or peptide analog sequence in a reversed order, namely, the amino acids are coupled in the peptide sequence in a reverse order to the amino acids order which appears in the native protein or in a specific peptide or analog identified as active. Whether completely or partially non-peptide, peptidomimetics according to this invention provide a spatial arrangement of chemical moieties that closely resembles the three-dimensional arrangement of groups in the peptide on which the peptidomimetic is based. As a result of this similar active-site structure, the peptidomimetic has effects on biological systems, which are similar to the biological activity of the peptide.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

"A peptide conjugate" according to the present invention, denotes a molecule comprising a sequence of a blood-vessel promoting peptide to which another moiety, either peptidic or non peptidic, is covalently bound, directly or via a linker.

The term "linker" denotes a chemical moiety, a direct chemical bond of any type, or a spacer whose purpose is to link, covalently, a cell-permeability moiety and a peptide or peptidomimetic. The spacer may be used to allow distance between the permeability-enhancing moiety and the peptide.

"Permeability" refers to the ability of an agent or substance to penetrate, pervade, or diffuse through a barrier, membrane, or a skin layer. A "cell permeability" or a "cell-penetration" moiety refers to any molecule known in the art which is able to facilitate or enhance penetration of molecules through membranes. Non-limiting examples include: hydrophobic moieties such as lipids, fatty acids, steroids and bulky aromatic or aliphatic compounds; moieties which may have cell-membrane receptors or carriers, such as steroids, vitamins and sugars, natural and non-natural amino acids, transporter peptides, nanoparticles and liposomes.

The term "physiologically acceptable carrier" or "diluent" or "excipient" refers to an aqueous or non-aqueous fluid that is well suited for pharmaceutical preparations. Furthermore, the term "a pharmaceutically acceptable carrier or excipient" refers to at least one carrier or excipient and includes mixtures of carriers and or excipients. The term "therapeutic" refers to any pharmaceutical, drug or prophylactic agent which may be used in the treatment (including 5 the prevention, diagnosis, alleviation, or cure) of a malady, affliction, disease or injury in a patient.

Pharmacology

Apart from other considerations, the fact that the novel active ingredients of the invention are peptides, peptide analogs or peptidomimetics, dictates that the formulation be suitable for delivery of these types of compounds. Although in general peptides are less suitable for oral administration due to susceptibility to digestion by gastric acids or intestinal enzymes novel methods are being used, in order to design and provide metabolically stable and oral bioavailable peptidomimetic analogs.

The pharmaceutical composition of this invention may be administered by any suitable means, such as orally, topically, intranasally, subcutaneously, intramuscularly, intravenously, intra-arterially, intraarticulary, intralesionally, by inhalation or parenterally, and are specifically formulated for the administration route. The compositions are formulated according to the administration route.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art (Pillai et al., Curr. Opin. Chem. Biol. 5, 447, 2001). Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (e.g. Fingl, et al., 1975, in "The Pharmacological Basis of Therapeutics", Ch. 1 p. 1).

The doses for administration of such pharmaceutical compositions range according to some embodiments of the present invention from about 0.1 mg/kg to about 50 mg/kg body weight.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

In certain embodiments, peptide delivery can be enhanced by the use of protective excipients. This is typically accomplished either by complexing the peptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy, 1998, Biotechnol. Prog. 14, 108; Johnson et al., 1996, Nature Med. 2, 795; Herbert et al., 1998, Pharmaceut. Res. 15, 357) a dry powder composed of biodegradable polymeric microspheres containing the protein in a polymer matrix that can be compounded as a dry formulation with or without other agents.

In certain embodiments, dosage forms of the compositions of the present invention include, but are not limited to, biodegradable injectable depot systems such as, PLGA based injectable depot systems; non-PLGA based injectable depot systems, and injectable biodegradable gels or dispersions. Each possibility represents a separate embodiment of the invention. The term "biodegradable" as used herein refers to a component which erodes or degrades at its surfaces over time due, at least in part, to contact with substances found in the surrounding tissue fluids, or by cellular action. In particular, the biodegradable component is a polymer such as, but not limited to, lactic acid-based polymers such as polylactides e.g. poly (D,L-lactide) i.e. PLA; glycolic acid-based polymers such as polyglycolides (PGA) e.g. Lactel® from Durect; poly (D,L-lactide-co-glycolide) i.e. PLGA, (Resomer® RG-504, 15 Resomer® RG-502, Resomer® RG-504H, Resomer® RG-502H, Resomer® RG-504S, Resomer® RG-502S, from Boehringer, Lactel® from Durect); polycaprolactones such as Poly(e-caprolactone) i.e. PCL (Lactel® from Durect); polyanhydrides; poly(sebacic acid) SA; poly(ricenolic acid) RA; poly(fumaric acid), FA; poly(fatty acid dimmer), FAD; poly(terephthalic acid), TA; poly(isophthalic acid), IPA; poly(p-{carboxyphenoxy}methane), CPM; poly(p-{carboxyphenoxy} propane), CPP; poly(p-{carboxyphenoxy}hexane)s CPH; polyamines, polyurethanes, polyesteramides, polyorthoesters {CHDM: cis/trans-cyclohexyl dimethanol, HD:1,6-hexanediol. DETOU: (3,9-diethylidene-2,4,8,10-tetraoxaspiro undecane)}; polydioxanones; polyhydroxybutyrates; polyalkylene oxalates; polyamides; polyesteramides; polyurethanes; polyacetals; polyketals; polycarbonates; polyorthocarbonates; polysiloxanes; polyphosphazenes; succinates; hyaluronic acid; poly(malic acid); poly(amino acids); polyhydroxyvalerates; polyalkylene succinates; polyvinylpyrrolidone; polystyrene; synthetic cellulose esters; polyacrylic acids; polybutyric acid; triblock copolymers (PLGA-PEG-PLGA), triblock copolymers (PEG-PLGA-PEG), poly (N-isopropylacrylamide) (PNIPAAm), poly (ethylene oxide)-poly (propylene oxide)-poly (ethylene oxide) triblock copolymers (PEO-PPO-PEO), poly valeric acid; polyethylene glycol; polyhydroxyalkylcellulose; chitin; chitosan; polyorthoesters and copolymers, terpolymers; lipids such as cholesterol, lecithin; poly(glutamic acid-co-ethyl glutamate) and the like, or mixtures thereof.

In some embodiments, the compositions of the present invention comprise a biodegradable polymer selected from, but not limited to, PLGA, PLA, PGA, polycaprolactone, polyhydroxybutyrate, polyorthoesters, polyalkaneanhydrides, gelatin, collagen, oxidized cellulose, polyphosphazene and the like. Each possibility represents a separate embodiment.

Fish Food Compositions

The food compositions of the present invention may be part of, or mixed with conventional of special fish food. Fish food normally consists of a feed used for the type of fish to be nourished and includes proteins, oils, vitamins and other additives.

According to some non-limiting examples, the antagonist compositions of the present invention are included in pelletized, solid compositions containing, about 15 to 50 percent protein or protein hydrolysate, about 2 to 5 percent fat, and about 3 to 10 percent crude fiber together with minor amounts of adjuvants, such as minerals, vitamins, and/or trace elements.

Fish food composition comprising the antagonists of the present invention are prepared using methods known in the art. For example, pellets, typically 0.5-20 millimeters in diameter, are made from the composition and dried prior to storage and use. The coherence of the pellets may be improved by dissolving a small amount of gelatin in the water. If water-soluble whey powder provides much of the protein content, the pellet surfaces are preferably coated with a little oil or fat to prevent premature disintegration of the pellets upon contact with water. Gelatin-bearing compositions may be foamed in a conventional manner to produce cellular pellets whose overall density is similar to that of water. Such pellets float in water and remain accessible to the fish for a relatively long period. Pellets that sink to the bottom are lost to many fish. The antagonists of the invention may also be mixed with commercial fish feed of conventional composition by uniformly distributing the addition in the basis composition and thereafter making pellets from the mixture obtained. According to some embodiments, food pellets are coated with the compounds of the invention and used for feeding the fish.

Although the present invention has been described with respect to various specific embodiments thereof in order to illustrate it, such specifically disclosed embodiments should not be considered limiting. Many other specific embodiments will occur to those skilled in the art based upon applicants' disclosure herein, and applicants propose to be bound only by the spirit and scope of their invention as defined in the appended claims.

EXAMPLES

The following examples demonstrate the in-vitro and in-vivo activity of the compounds of the present invention as antagonists of fish NKB.

Example 1: Design and Synthesis of Peptidomimetics

Some of the peptidomimetic of the present invention were design based on the following considerations:
i) The N-terminus of the peptide was modified by adding a capping moiety such as succinyl (succ) coupled to the Asp residue, such that the peptide lacks the terminal amino group that is susceptible to degradation by amino peptidases. This unexpectedly resulted in ability of shortening of the active peptide from 11 to 7 amino acids;
ii) Replacement of a Phe residue by D-Trp prevented tight fitting of the agonist to the NK receptor. This altered the activity of the peptide from agonist into antagonist and also stabilized the peptide to degradation by endopeptidases.
iii) The Val residue was N-methylated to impose conformational constrain that stabilize the bioactive conformation thus impose receptor selectivity and metabolic stability, preventing degradation by endopeptidases.
iv) The residue Gly was replaced by βAla (betta alanine) resulting in increased conformational flexibility of the bioactive conformation and facilitate the conversion of agonist into antagonist.
v) The carboxamide group in the carboxy terminus is essential for binding and receptor activation and prevents degradation by carboxypeptidases.

The peptidomimetic were synthesized by an automatic solid-phase method applying Fmoc active-ester chemistry. Difficult coupling of hydrophobic amino acids, such as Fmoc-D-Trp-OH to NMe-Val-peptidyl-resin was performed twice using HATU for 5 hours in DMF. The compounds were purified by HPLC to >95% purity.

Example 2: In Vitro Tests

There are two signal transduction pathways, one is relayed trough cAMP/PKA (protein kinase A), and the second is trough Ca2+/PKC. The PKA pathway is activated by CRE (cAMP response element) and the PKC through SRE (steroid response element).

In order to differentiate between the PKC and PKA signal transduction pathways, a sensitive luciferase (LUC) reporter gene assay was utilized by using the LUC transcriptionally regulated by a serum response element (SRE; Invitrogen) or cyclic AMP (cAMP) response element (CRE; Invitrogen). Tilapia tac3ra and tac3rb (GenBank accession numbers KF471674 and KF471675, respectively) or zebrafish tac3ra and tac3rb (JF317292, and JF317293, respectively) were cloned in pcDNA3.1 expression vector (Zeo-; Invitrogen) under the control of the CMV promoter.

Transient transfection, cell procedures and stimulation protocols were generally according to (Levavi-Sivan et al., 2005, Mol Cell Endocrinol 236:17-30; Biran et al., 2008, ibid, Biran et al., 2012, ibid, Biran et al., 2014 ibid). Briefly, COS-7 cells were grown in DMEM supplemented with 10% FBS, 1% glutamine, 100 U/ml penicillin, and 100 mg/ml streptomycin (Biological Industries) under 5% CO2 until confluent. Cotransfection of either pc-tac3ra, pc-tac3rb (at 3 μg/plate), a reporter plasmid (at 2 μg/plate), and pCM.

Transfection was carried out with FuGENE 6.0 reagent (Roche). The cells were serum starved for 36 h, stimulated with vehicle or various concentrations of either human NKB, tilapia NKB, tilapia NKF, zebrafish NKBa, NKBb or zebrafish NKF for 6 h, and then harvested and analyzed.

Lysates prepared from the harvested cells were assayed for both luciferase activity and β-galactosidase activity, which was used as an internal standard to normalize the luciferase activity directed by the test plasmid, as described previously. Transfection experiments were performed in triplicate with three independently isolated sets.

The concentrations of ligand used were from 1 nM to 1 μM. Treatments were performed in quadruplicate in three independent experiments.

Each antagonist was added at different concentrations with a constant concentration of the wild-type NKB or NKF, at a dose of the ligand ($10^{-8}$M) that gave a response close to the ED50. The results were analyzed by Prism software, according to a non-linear regression one-site competition curve.

Figure 1B:
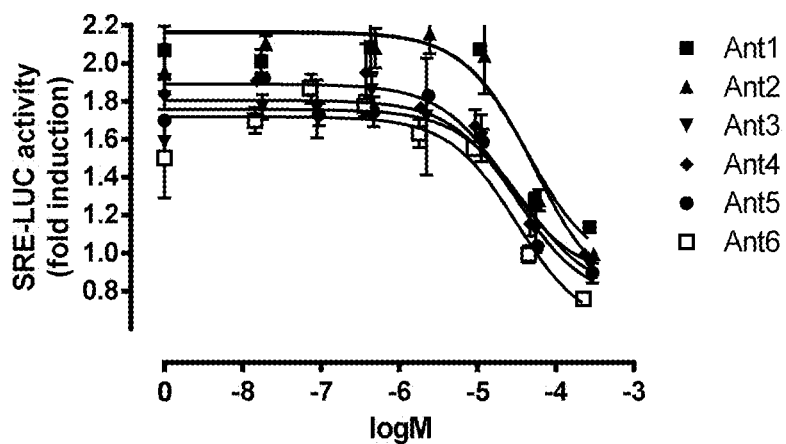
Figure 1C:
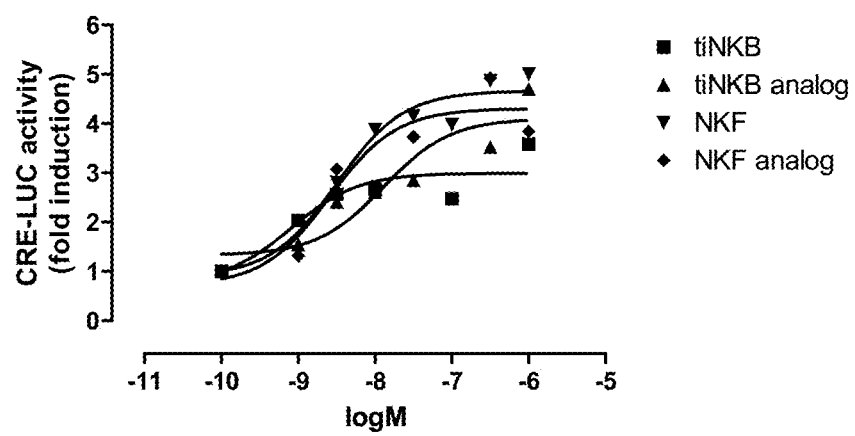
FIG. 1C demonstrates in comparison, agonist activity of various NKB and NKF analogs in the CRE activation model.

The effect of NKB antagonists was tested in tilapia when each antagonist was added at different concentration concomitantly with NKB at $10^{-8}$ M (=0.1 nM). Tilapia NKB increased the luciferase activity by 1.8 fold. The various antagonists reduced this response by approximately 60% (FIG. 1A). Similar results were obtained using the SRE response (FIG. 1B). In contrast, Tilapia NKB and NKF analogs (disclosed in WO 2013/018097) were shown to have agonistic activity in both assays as demonstrated in FIG. 1C for the CRE assay.

Figure 2A:
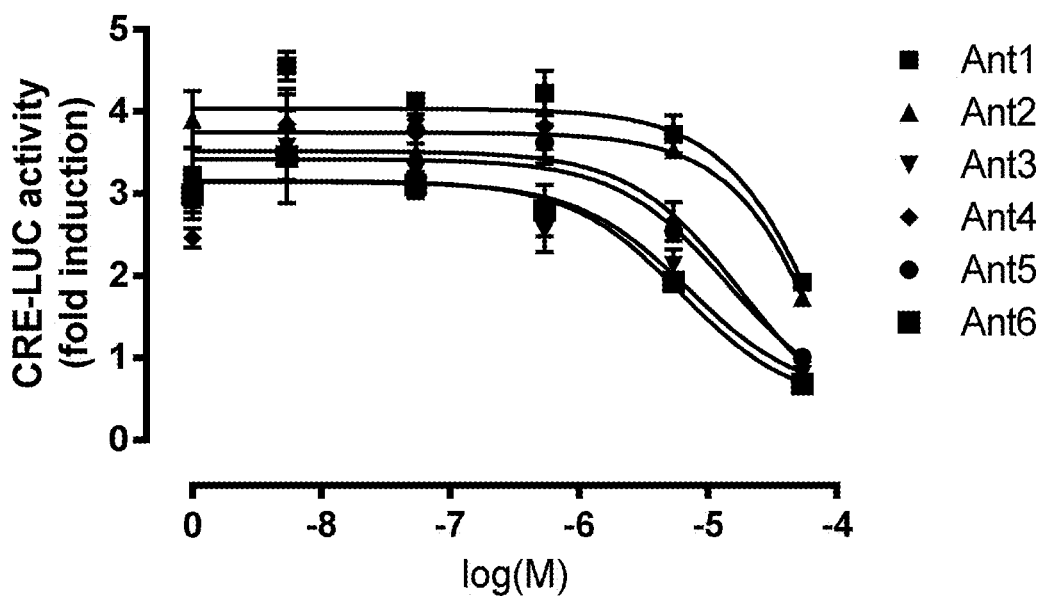
FIGS. 2A and 2B shows the effect of six peptidomimetics in inhibiting signal transduction in zebrafish (FIG. 2A CRE activation, FIG. 2B SRE activation). Zebrafish NKB increased the signal transduction activity by more than 3 fold. The effect of the peptidomimetics was tested when each antagonist was added at different concentration concomitantly with NKB at $1*10^{-8}$ M (=0.1 nM).
Figure 2B:
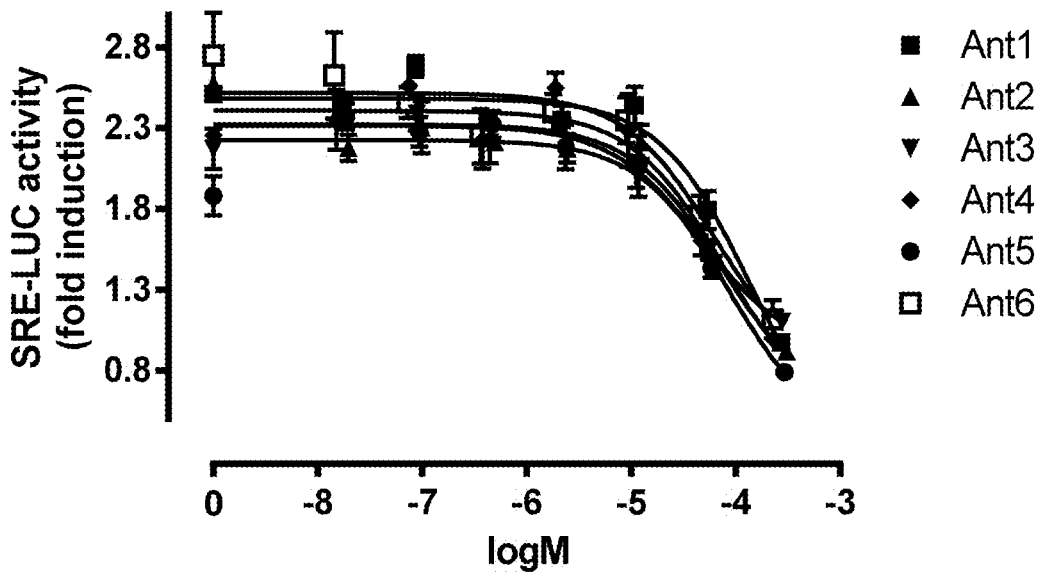

The zebrafish NKB was more efficient than the tilapia peptide in the induction of the signal transduction activity, and increased the CRE-LUC by more than 3 fold. The effect of NKB antagonists was tested when each antagonist was added at different concentration concomitantly with NKB at $10^{-8}$ M (=0.1 nM). The various antagonists reduced the response by approximately 60% (FIG. 2A). Similar results were obtained using the SRE response (FIG. 2B), while NKB agonists were not inhibitory but stimulatory and gave results similar to FIG. 1C.

To conclude, NKB antagonist peptidomimetics according to the present invention are able to inhibit the NKB signal transduction.

Example 3. Non-Peptide Antagonists for NKB

The effect of known NKB small molecule antagonists was tested in vitro and in vivo. The compounds are: SB-222200 (Sarau et al., 2000 ibid); Osanetant (SR-142,801) and talnetant (SB 223412, (Sarau et al., 1997 ibid).

The effect of the NKB antagonist SB222200 on CRE-Luc in COS-7 cells transfected with tilapia tac3r was tested when the human receptor and ligand served as a positive control.

Figure 3A:
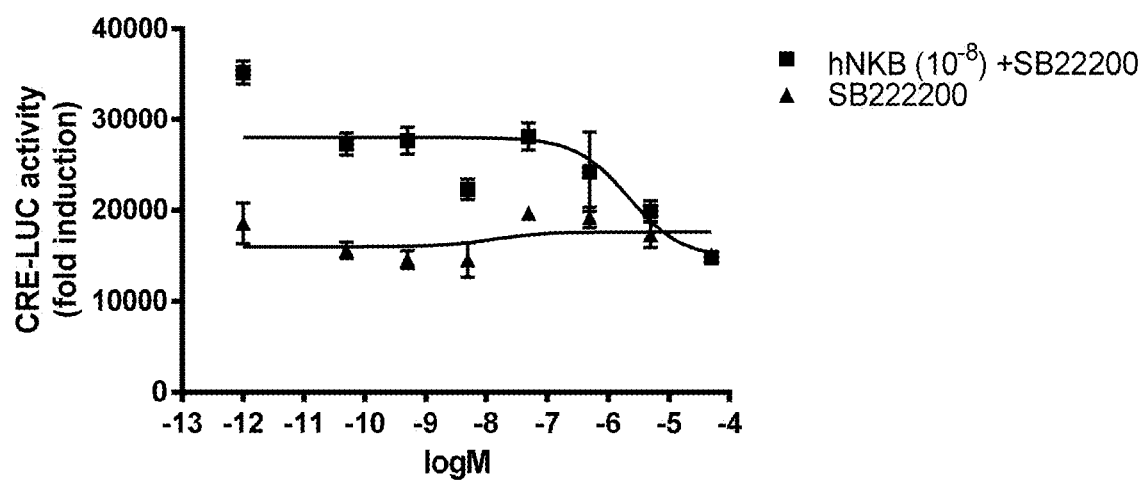
FIGS. 3A and 3B demonstrate the effect of the NKB antagonist SB222200 on CRE-Luc in COS-7 cells transfected with tilapia tac3r, using the human receptor and ligand as positive control.

As shown in FIG. 3A, the non-peptide antagonist alone had no effect on the luciferase activity, while hNKB, tilapia NKB or tilapia NKF, at 0.1 nM (=$10^{-8}$ M), increased the luciferase activity by 1.7 and 2.3 fold, respectively.

Figure 3B:
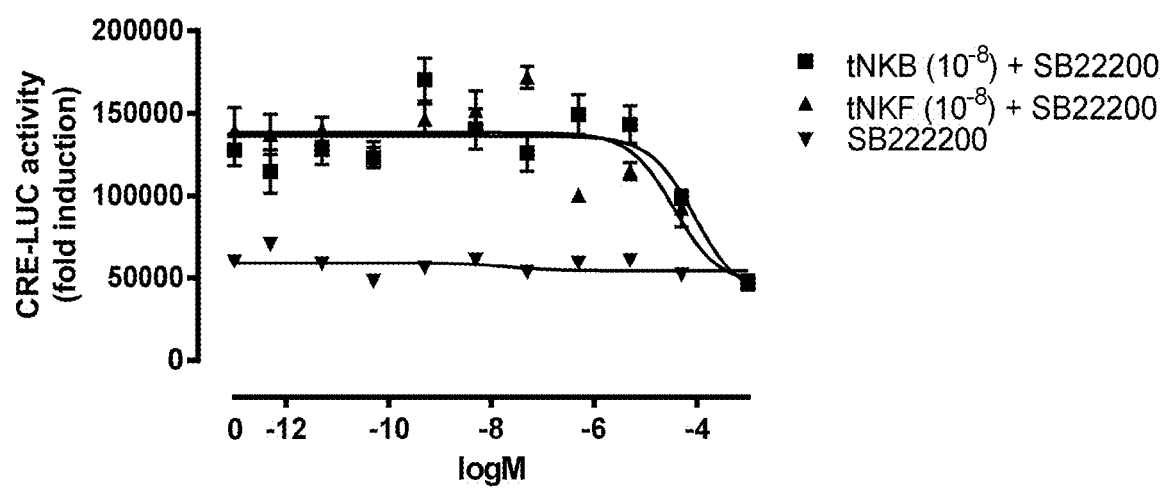

When different concentrations of the antagonist were added concomitantly with 0.1 nM of the native ligands (NKB or NKF) a typical inhibition curve was achieved, demonstrating the antagonistic potency of SB222200 on the tilapia NKB receptor (FIG. 3B).

Figure 4A:
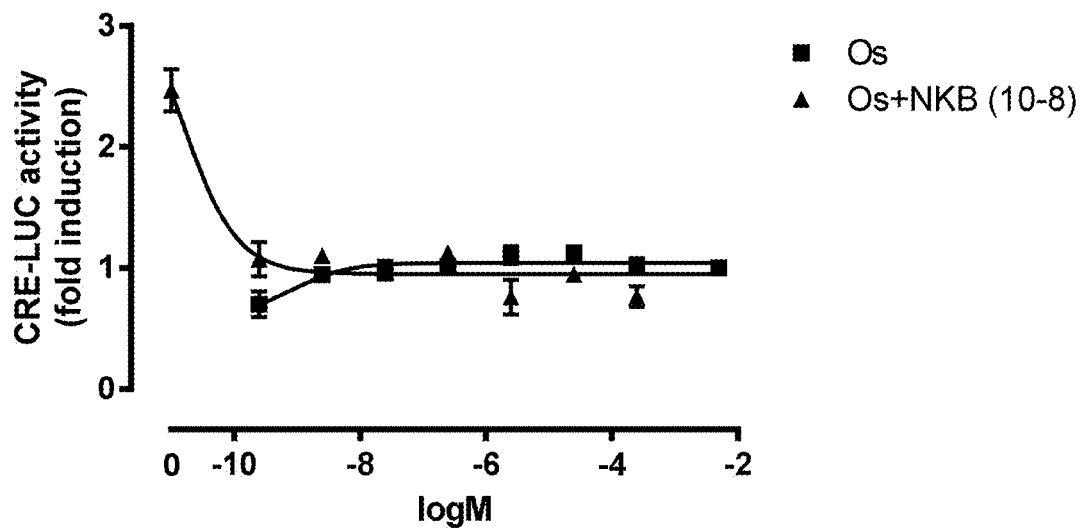
FIGS. 4A and 4B describe the effect of the NKB antagonist Osanetant (SR-142,801) on CRE-Luc in COS-7 cells transfected with tilapia tac3r when the human receptor and ligand serve as positive control.
Figure 4B:
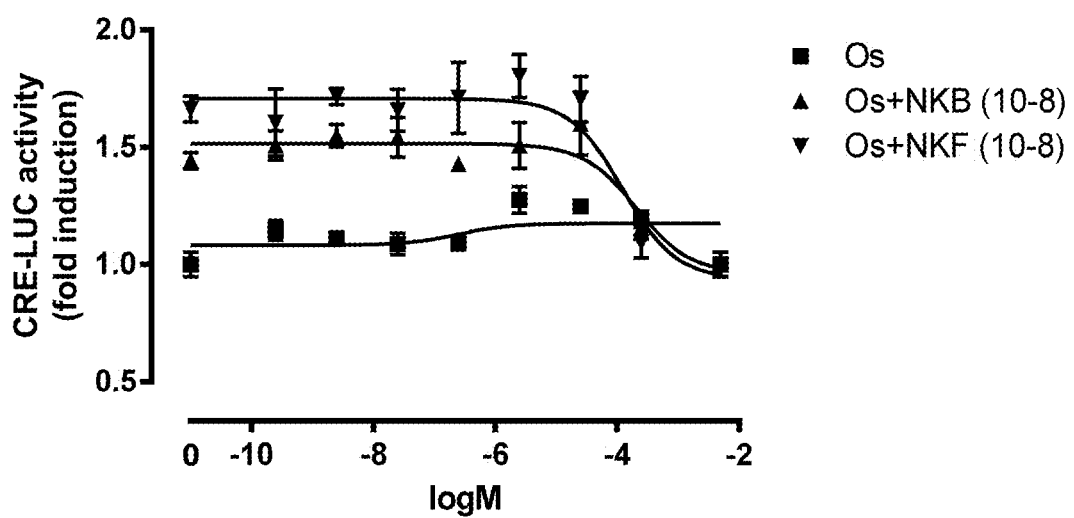

The effect of the NKB antagonist Osanetant (SR-142,801) was tested on CRE-Luc in COS-7 cells transfected with tilapia tac3r when the human receptor and ligand served as a positive control. The non-peptide antagonist alone had no effect on the luciferase activity while hNKB, tilapia NKB or tilapia NKF, at 0.1 nM (=$10^{-8}$ M), increased the luciferase activity by 2.5 and 1.6 fold, respectively (FIG. 4A). However, when different concentrations of the antagonist were added concomitantly with 0.1 nM of the native ligands (NKB or NKF) a typical inhibition curve was achieved, showing the antagonistic potency of Osanetant (SR-142, 801) on the tilapia NKB receptor (FIG. 4B).

Figure 5A:
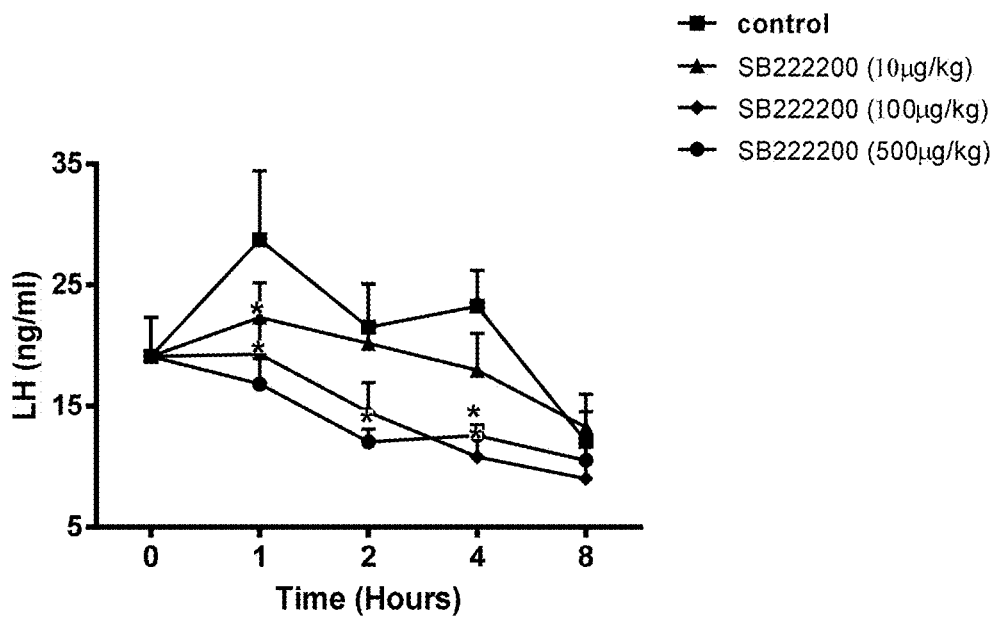
FIGS. 5A and 5B depicts the results of in vivo experiments testing the NKB antagonistic activity of SB222200 (at 10, 100 or 500 μg/kg body weight) on FSH (FIG. 5A) and LH (FIG. 5B) release in tilapia.
Figure 5B:
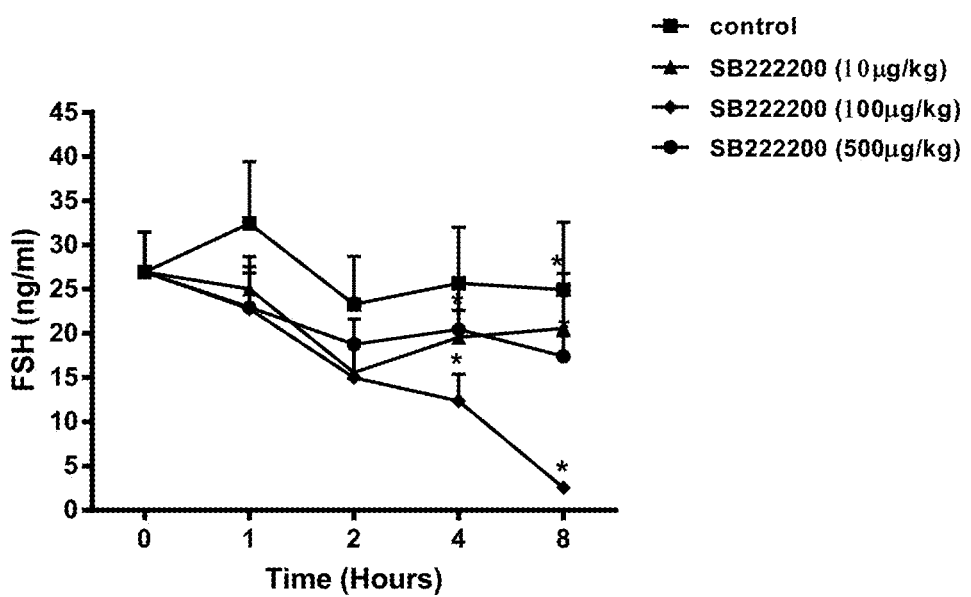

SB222200 was further tested in vivo for its NKB antagonistic activity on gonadotropin release in tilapia. Sexually mature tilapia females (0.62±0.22%; n=10/treatment) were injected with different doses of the NKB non-peptide antagonist SB222200 (10, 100 or 500 µg/kg body weight) at time 0. 1, 2, 4 and 8 hours after the injection the fish were bled from their caudal vasculature. The levels of the gonadotropins FSH and LH were determined using specific ELISA according to Aizen et al., 2007 (Aizen et al., 2007, Gen Comp Endocrinol, vol. 153, pp 323-332). The results show that while no significant changed were recorded in the control group, a significant gradual decline was recorded in both FSH (FIG. 5A) and LH (FIG. 5B) levels starting already 1 hour after the injection.

Example 4. In Vivo Experiments

Selected antagonists that were shown effective in the in-vitro transactivation assay are tested in vivo.

Adult male Tilapia (BW 90 g) were injected ip with saline and 25% DMSO, SB2222000, or the NKB antagonists Ant-4 (500 µg/kg BW every 48 h for 2 weeks, n=fish per group). The fish were bled from the caudal blood vessels into heparinized syringes every 2 days after injection. At days 7 and 14 five fish from each group were bled, striped for sperm volume and gonads were taken for Histology. Plasma was analyzed for LH, FSH and 11KT. Blood samples were collected from the caudal vasculature and centrifuged (3000 rpm for 20 minutes at 4° C.) to obtain plasma samples, which were stored at −20° C. until assayed, ELISAs were performed according to (Aizen et al., 2007, Gen Comp Endocrinol, vol. 153, pp 323-332) for FSH and LH and according to Hurvitz et al., 2005 (Gen Comp Endocrinol 140:61-73) for 11KT 1-ketotestosterone, the main androgen in fish which is involved in spermatogenesis).

Figure 6:
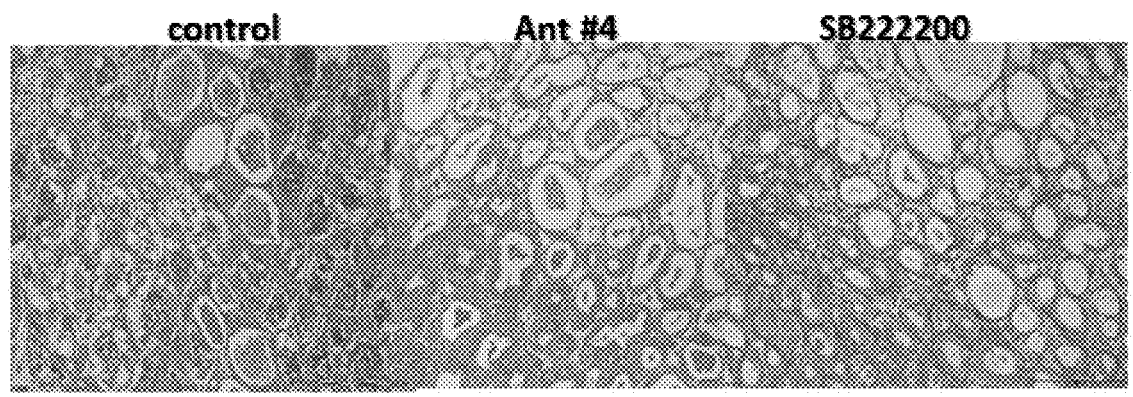
FIG. 6 represents histological observations of gonads from testes of treated fish versus control fish. Fish testes are organized in cysts.
Figure 7:
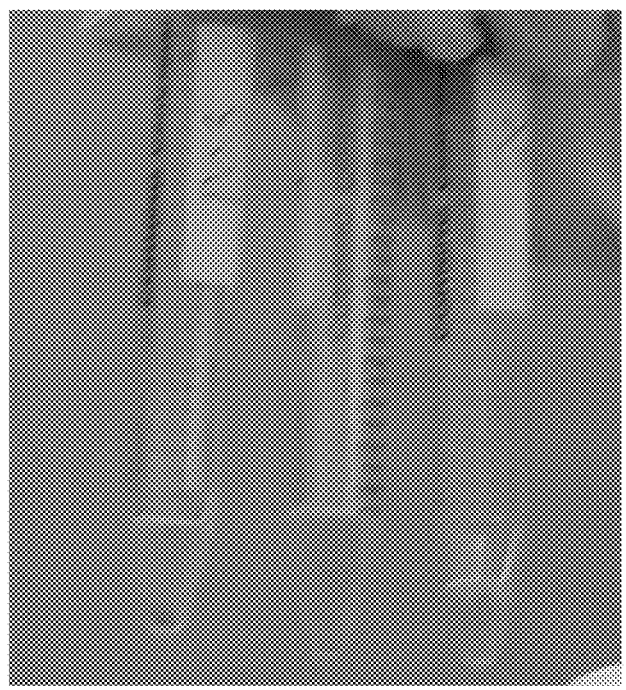
FIG. 7 semen volume of fish injected with NKB antagonists SB222200, NKB-antagonist Ant-4, or control.
Figure 8:
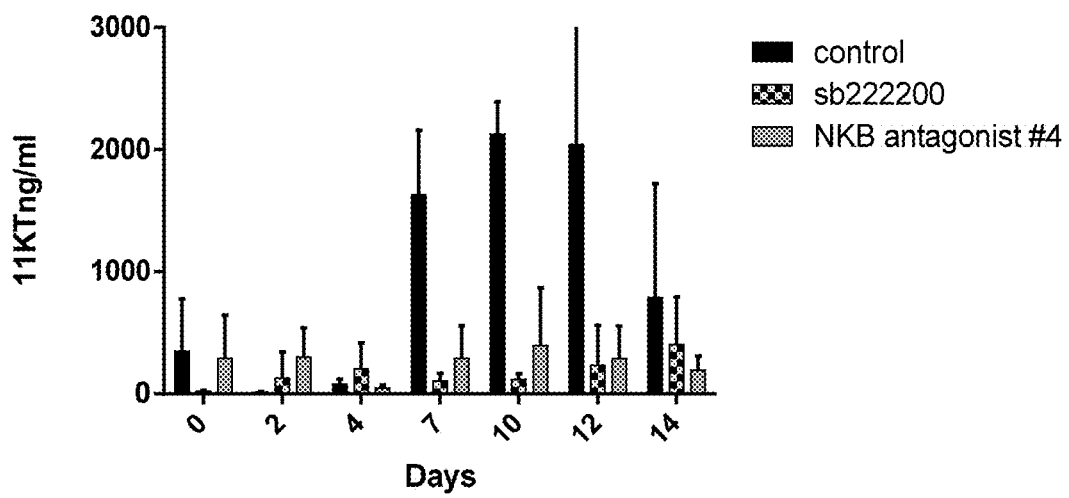
FIG. 8 11-ketotestosterone (11KT) levels in fish injected with SB222200 or NKB-antagonist Ant-4 for 14 days.

FIG. 6 represents histological observations of gonads from testes of treated fish versus control fish. Fish testes are organized in cysts. As demonstrated in the figure, Fish exposed to NKB-antagonist Ant-4 contained more partially empty cysts with mature spermatozoa (mature sperm). Semen volume of fish injected with NKB antagonists is presented in FIG. 7. From right to left: semen from fish injected with SB222200; semen from control fish; semen from fish injected with NKB-antagonist #4. 11KT levels in fish injected with SB222200 or NKB-antagonist Ant-4 are shown in FIG. 8. 11KT is the main androgen in fish and is involved in spermatogenesis. During the treatment period, plasma 11KT levels increased gradually from 0 to 12 days for the control fish, whereas for fish that were injected with SB222200 or NKB-antagonist Ant-4 (#4), this increase was significantly inhibited.

Example 5. In-Vivo Growth of Tilapia

Figure 9:
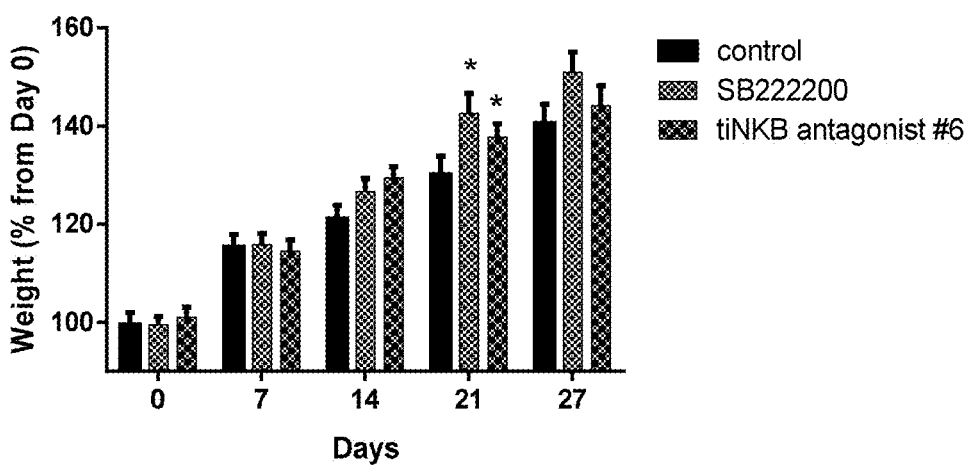
FIG. 9 growth rates of adult male tilapia in response to injection of SB2222000, or NKB antagonists Ant-6 (500 μg/kg BW every 48 h for 2 weeks, n=25 fish per group).

Adult male tilapia (BW 60 g) were injected ip with saline and 25% DMSO, SB2222000, or NKB antagonists Ant-6 (500 µg/kg BW every 48 h for 2 weeks, n=25 fish per group). Fish were weighed every 7 days. As indicated in FIG. 9, significant growth was seen at day 21, seven days after the treatment was finished.

Figure 10:
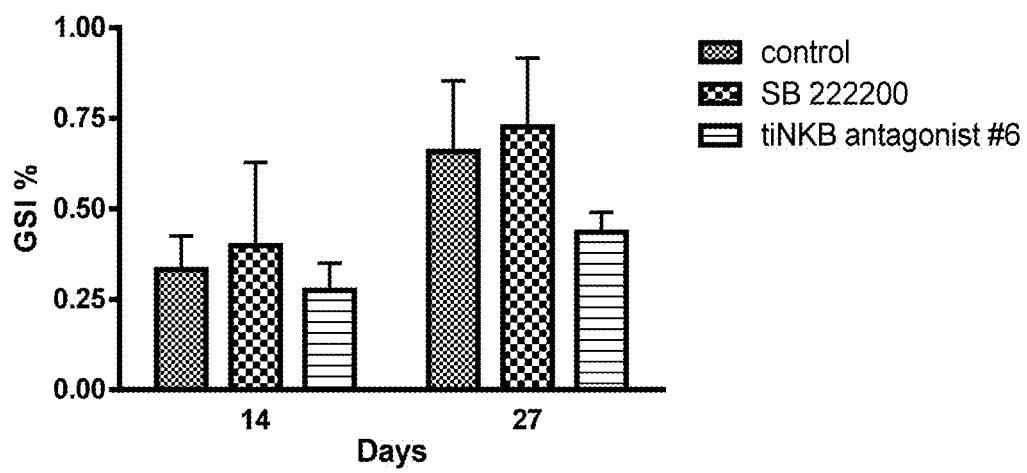
FIG. 10—Gonado-somatic-index (GSI) of fish injected with either SB222200 or NKB-antagonist Ant-6.
Figure 11:
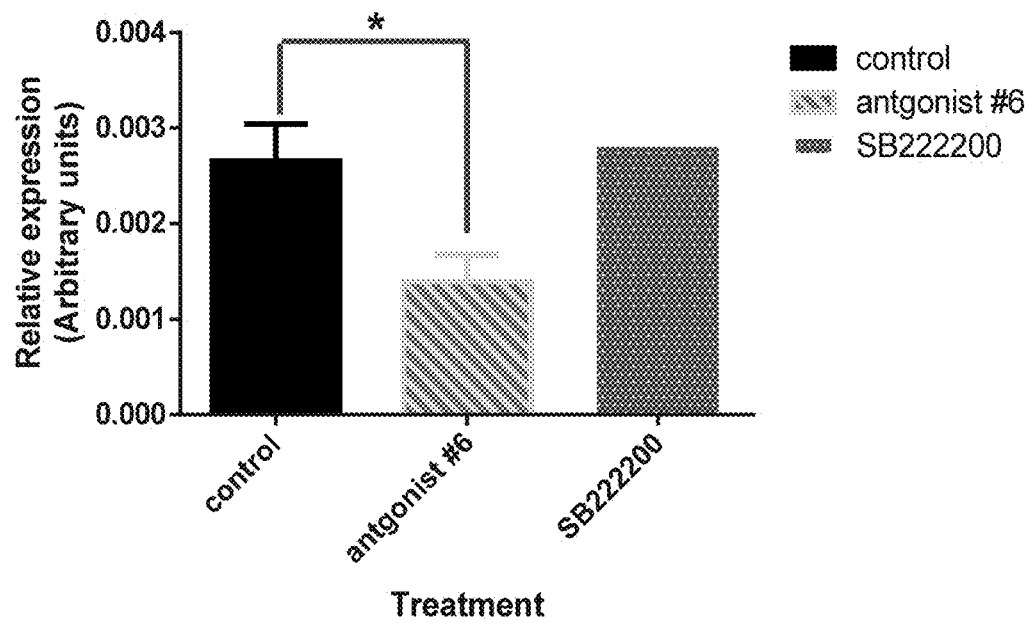

The gonadosomatic index (GSI), is the calculation of the gonad mass as a proportion of the total body mass. The GSI value of the injected fish was also calculated (FIG. 10). At day 27, fish were sacrificed and total RNA was extracted from their testes. Proliferating cell nuclear antigen (PCNA) is a DNA clamp that acts as a factor for DNA polymerase δ in eukaryotic cells and is essential for replication. The gene expression of PCNA was determined in the testes of the injected fish after 27 days (FIG. 11).

Example 6. Feeding of Young Tilapia

Figure 12A:
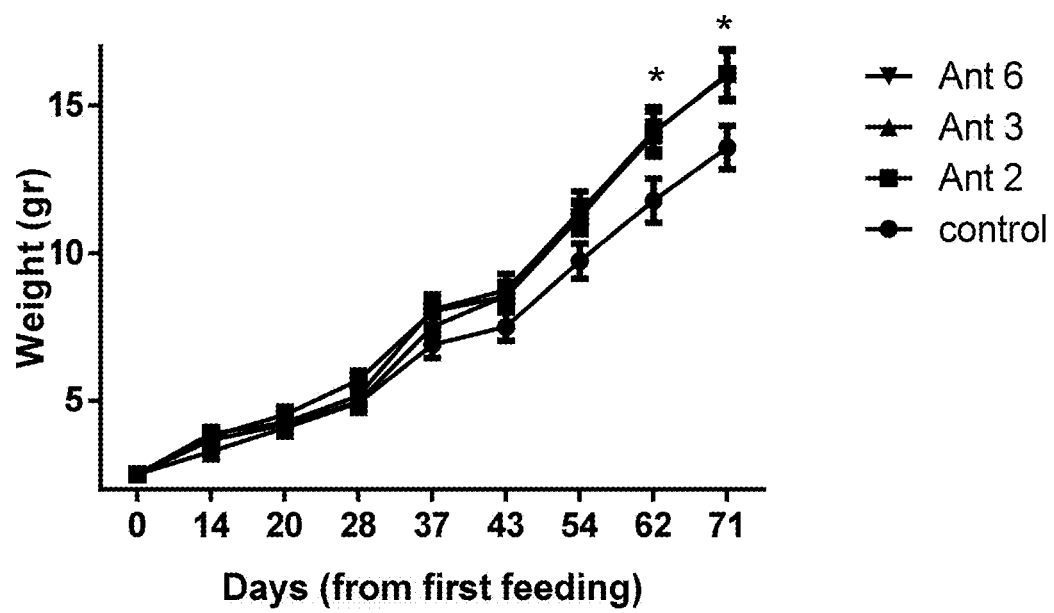
FIGS. 12A and 12B growth in response to feeding of young fish with antagonists.
Figure 12B:
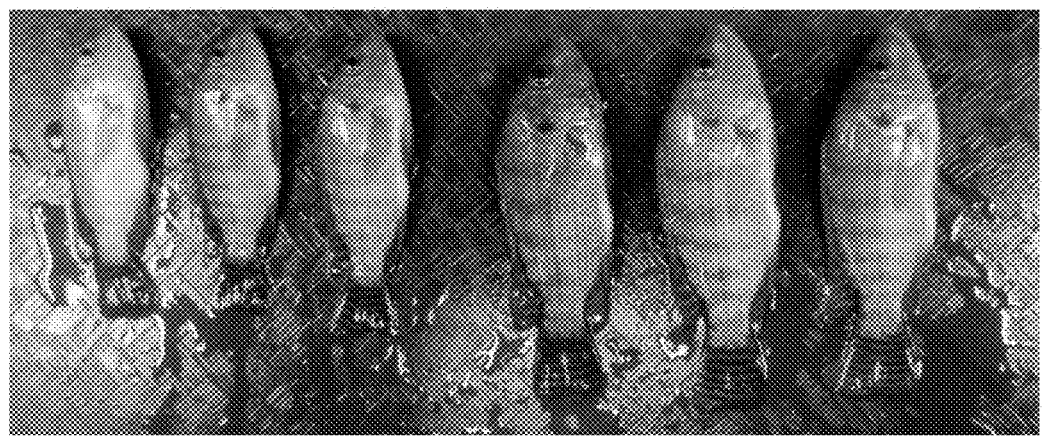

Female tilapia fish at age 105 days were used in this study. Feeding, by fish pellets coated with the peptidomimetics antagonists, was initiated at age of 3 month and 12 days. The diet of NKB antagonists (Ant-2, Ant-3, Ant-6) was applied at 7.5 mg/kg feed (2% to 3% of fish weight). The fish were fed twice daily during the day light hours. Fish growth rate was determined. As indicated in FIGS. 12A and 12B fish that were fed on a diet containing the NKB antagonists grew significantly faster (about 25% increase in body weight) than the control fish. No changes were observed in their internal organs (as determined by photography of the organs).

Example 7. In Vitro Experiments in Salmon

Similar to the in-vitro experiments performed in Example 2 in Tilapia and Zebrafish, the inhibition of NKB activity was tested in Salmon fish. Salmon tac3 receptor was cloned in pcDNA3.1 expression vector (Zeo-; Invitrogen) under the control of the CMV promoter. Transfection was carried out with FuGENE 6.0 reagent (Roche). The cells were serum starved for 36 h, stimulated with vehicle or various concentrations of either tilapia NKB for 6 h, and then harvested and analyzed. Lysates prepared from the harvested cells were assayed for both luciferase activity and β-galactosidase activity, which was used as an internal standard to normalize the luciferase activity directed by the test plasmid. Transfection experiments were performed in triplicate with three independently isolated sets. The concentrations of ligand used were from 1 nM to 1 µM. Treatments were performed in quadruplicate in three independent experiments. Each antagonist (NKB-ant 4 and NKB-ant 6) was added at different concentrations with a constant concentration of the wild-type NKB ($10^{-8}$M) that gave a response close to the ED50. The results were analyzed by Prism software, according to a non-linear regression one-site competition curve.

Figure 13:
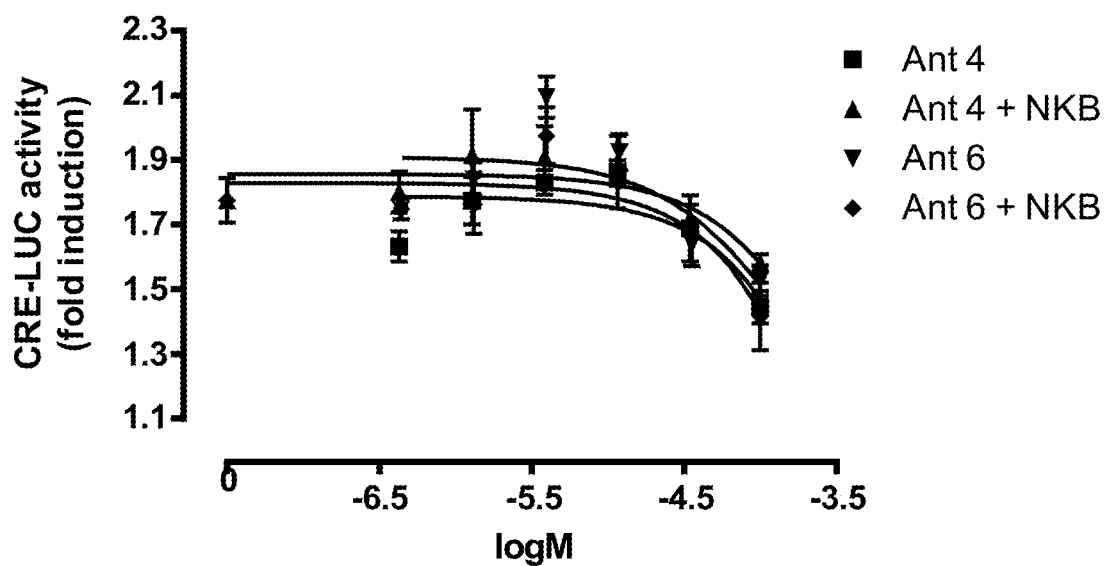
FIG. 13 shows the effect of the NKB antagonist No. 4 and No 6, on CRE-Luc in COS-7 cells transfected with salmon tac3r.

When salmon tac3 was transfected, NKB increased the luciferase activity by 1.8 fold. As demonstrated in FIG. 13, both antagonists #4 and #6 successfully reduced this response by approximately 60%.

Example 8. In Vitro Efficacy in Salmon

Figure 14:
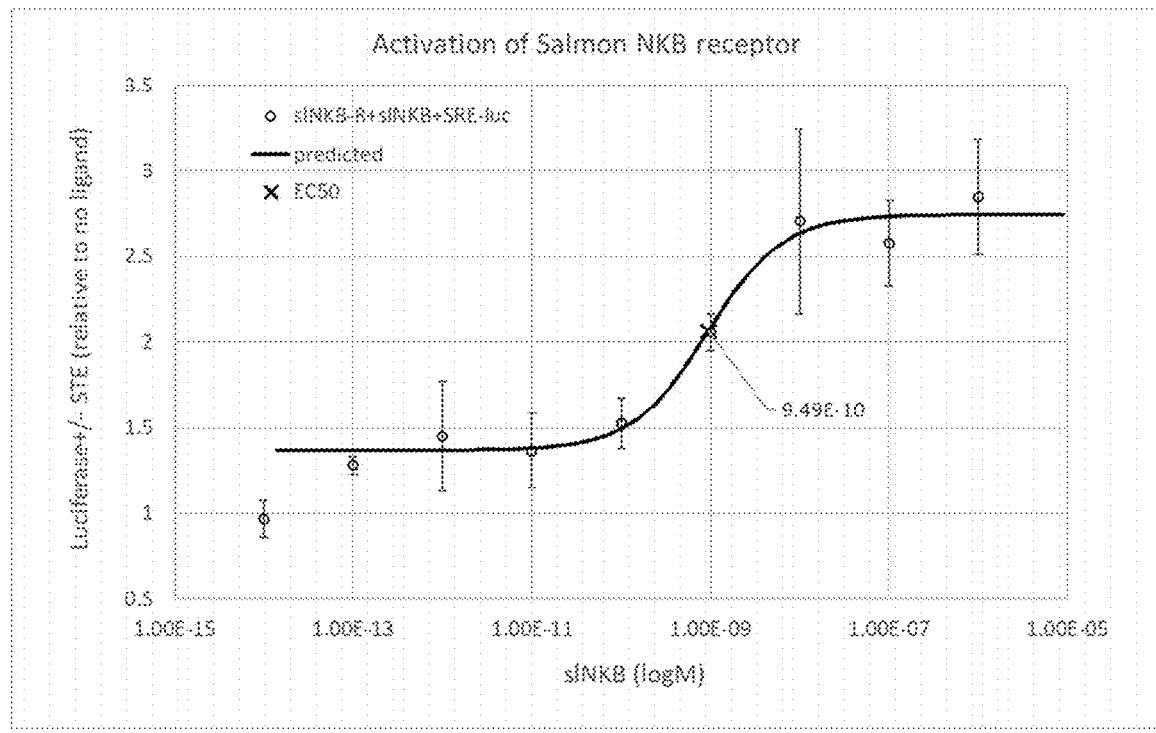
FIG. 14 demonstrates a dose depended luciferase activity (dots) in response to increasing concentration of salmon NKB (slNKB) ligand in COST cells expressing salmon NKB receptor (slNKBr) and SRE-Luc reporter (indicating intercellular PKC signaling). The predicted EC50, calculated according to Quatric regression fit, is shown.
Figure 15A:
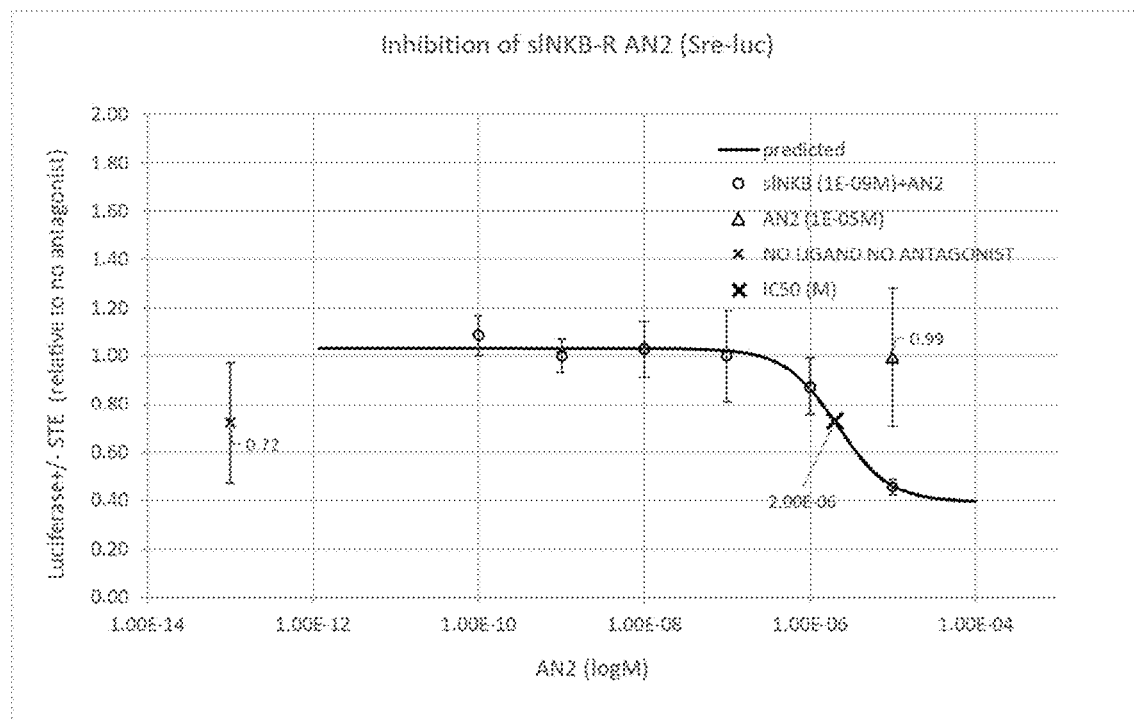
FIG. 15 A-D are graphs from in vitro experiments performed in the cell system of FIG. 14, using the compounds Ant-6 (a), Ant-3 (b), Ant-2 (c), and the known KNB antagonist SB22000 as a positive control (d). All results are relative to maximal receptor activation (ligand treatment without antagonist)±SEM.
Figure 15B:
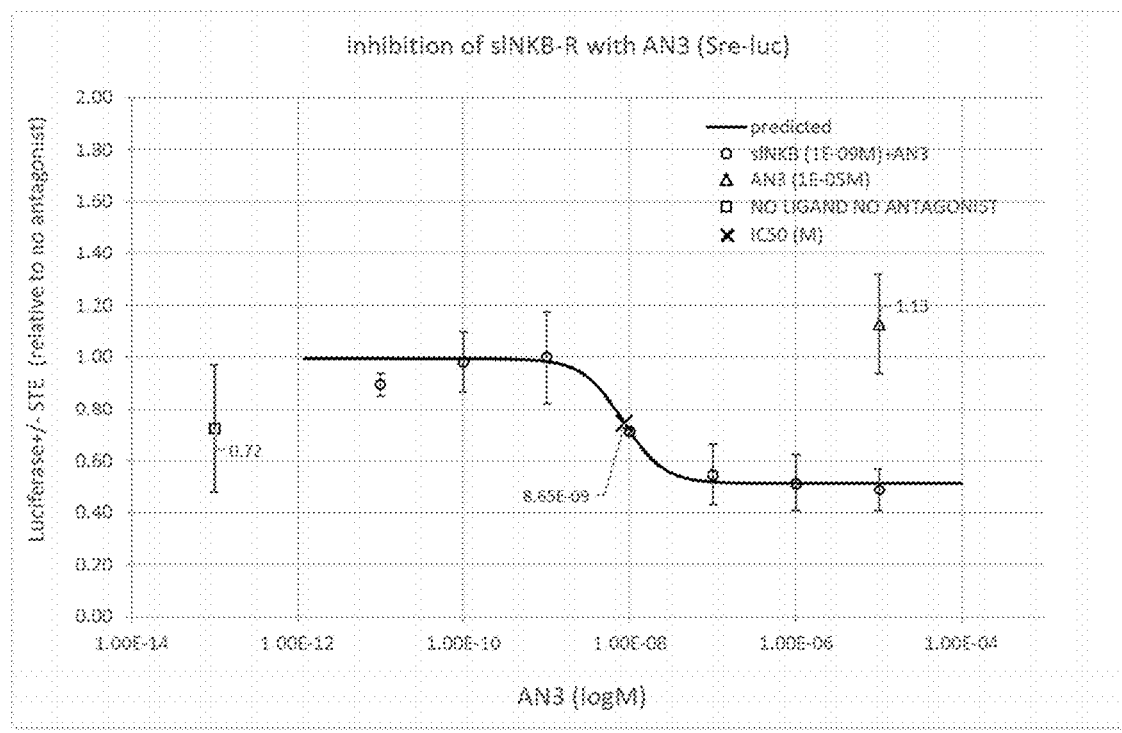
Figure 15C:
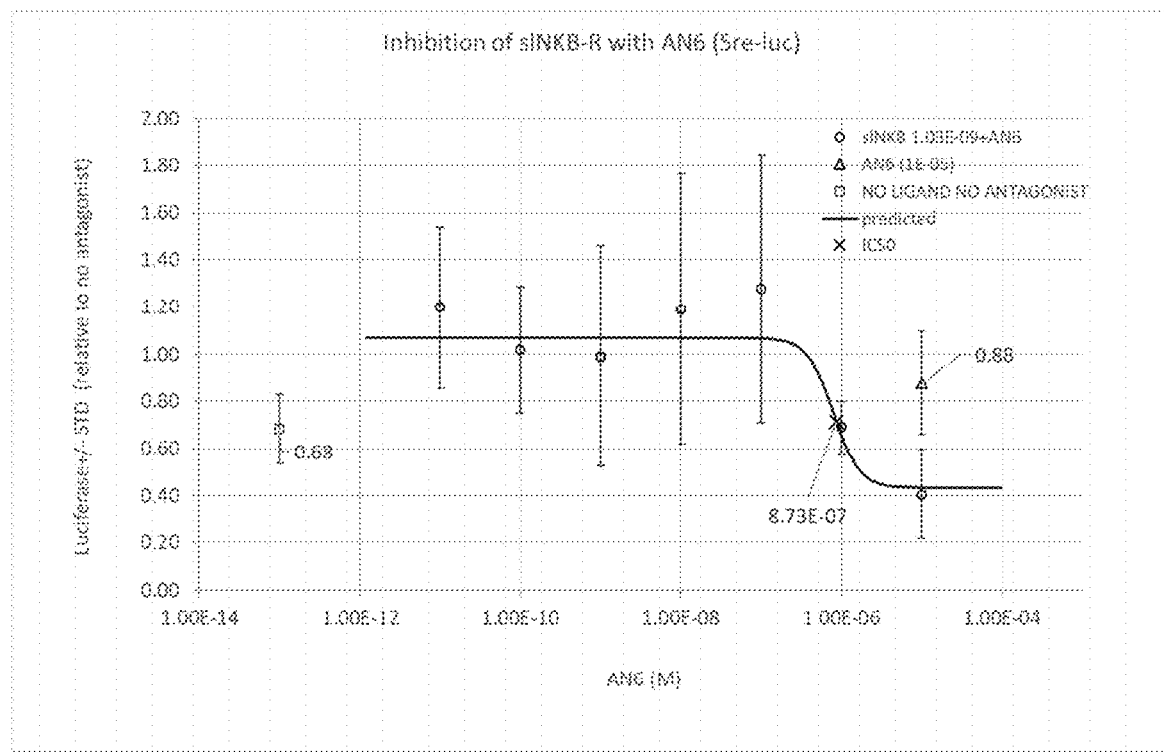
Figure 15D:
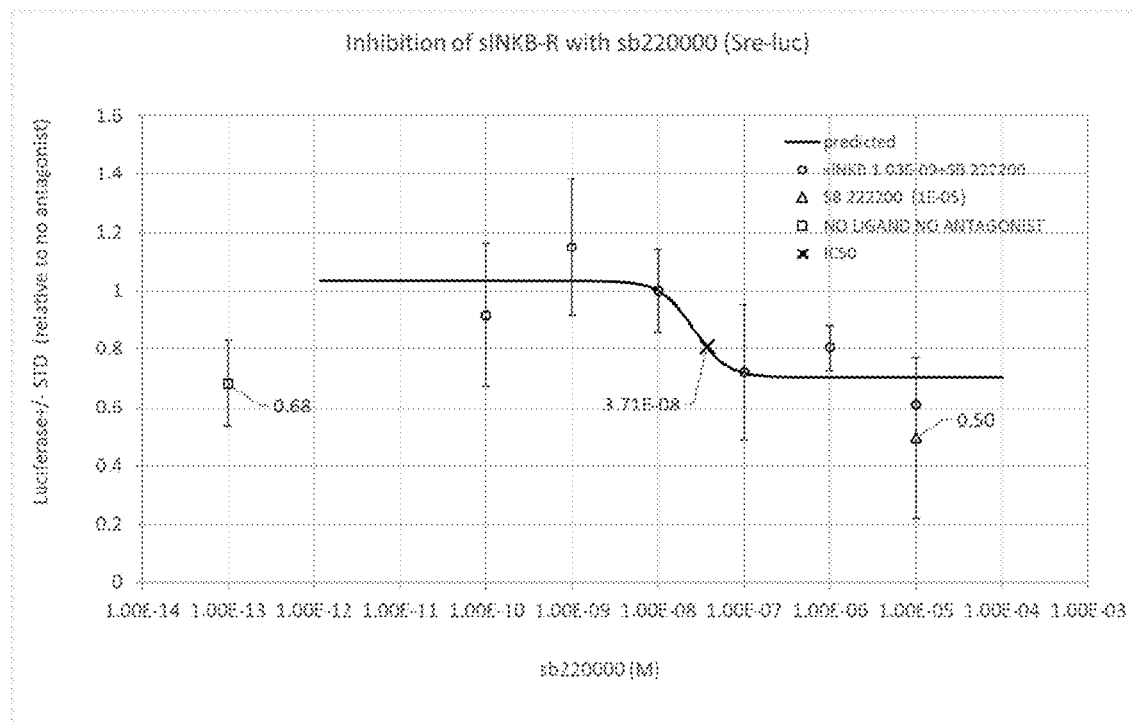

In order to test the potential activity of these unique antagonists in salmon NKB (slNKB), a cell system was designed to determine the activation efficiency of slNKB and compare and determine inhibitory efficiency of the different antagonists.

slNKB receptor was co-expressed with SRE-Luciferase (Luc) reporter (intercellular PKC signaling) in COS7 cells. Cells were treated with increasing concentration of Salmon NKB (slNKB) ligand. As shown in FIG. 14, cells treated with increasing concentration of slNKB ligand showed a dose-depended luciferase activity. The results were used to calculate the half maximal effective concentration (EC50=1.03E−09M).

Cells were then co-treated with slNKB and increasing concentrations of the compounds of SEQ ID Nos. 2, 3 and 6 (Ant 2, 3, 6) and SB22000 (a small molecule KNB antagonist, as a positive control) Inhibition factor at 50% (IC50) was calculated from these results. As demonstrated in FIGS. 15 A-D, the compounds ANT 2, 3, 6 and SB22000 shows significant dose-depended inhibition with IC50 of 2.6 µM, 6.16 nM, 0.87 µM and 37 nM respectively.

The invention claimed is:

1. A peptidomimetic of 6-10 amino acid residues comprising the sequence $X^1$-NMeVal-βAla-Leu-Met-Z (SEQ ID NO: 7), wherein $X_1$ consists of 2 or 3 amino acid residues comprising an aromatic residue, a negatively charged acidic residue, and optionally an N-terminal capping moiety or modification; and Z represents the C-terminus of the peptide which may be amidated, acylated, reduced or esterified.

2. The peptidomimetic of claim 1, wherein $X_1$ comprises an N-terminal capping moiety.

3. The peptidomimetic of claim 1, wherein $X_1$ consists of 2 or 3 amino acids and an N-terminal capping moiety.

4. The peptidomimetic of claim 3, wherein the N-terminal capping moiety is selected from the group consisting of: succinyl, oxalyl, malonyl, glutaryl, adipoyl, pimaloyl pimeloyl, suberoyl, and acetyl.

5. The peptidomimetic of claim 1, comprising an amidated C-terminus.

6. The peptidomimetic of claim 1, comprising an amidated C-terminus and an N-terminal capping moiety.

7. The peptidomimetic of claim 1, consisting of 6-7 amino acid residues and an N-terminal capping moiety.

8. The peptidomimetic of claim 1, wherein $X_1$ is selected from the group consisting of: Succ-Asp-Phe; Succ-Asp-Ser-Phe; and Succ-Asp-Ser-DTrp, wherein Succ denotes a succinyl.

9. The peptidomimetic of claim 1 selected from the group consisting of:

(SEQ ID NO: 2)
Succ-Asp-Phe-N(Me)Val-βAla-Leu-Met-NH₂;

(SEQ ID NO: 3)
Succ-Asp-Ser-Phe-N(Me)Val-βAla-Leu-Met-NH₂;

(SEQ ID NO: 4)
Succ-Asp-Ile-D-Trp-N(Me)Val-βAla-Leu-Met-NH₂;
and (SEQ ID NO: 6)
Succ-Asp-Ser-DTrp-N(Me)Val-βAla-Leu-Met-NH₂;

wherein Succ denotes a succinyl.

10. A food composition comprising at least one peptidomimetic according to claim 1.

11. The food composition of claim 10, wherein the at least one peptidomimetic is selected from the group consisting of SEQ ID NO: 2, SEQ ID NO: 3, SEQ ID NO: 4, and SEQ ID NO: 6.

12. The food composition of claim 10, comprising at least one nutrient.

13. The food composition of claim 10, comprising at least one food additive.

14. The food composition of claim 10, formulated for administration to fish as part of regular food or water consumption.

15. A Pharmaceutical composition comprising at least one peptidomimetic according to claim 1 and at least one acceptable carrier, diluent, salt or excipient.

16. The pharmaceutical composition of claim 15 formulated for administration to fish by a route selected from the group consisting of: intraparietal administration, oral administration and administration by immersion.

17. A method of inhibiting at least one parameter of fish reproduction or maturation, the method comprising administering to fish a food or a pharmaceutical composition comprising at least one peptidomimetic according to claim 1.

18. The method of claim 17 wherein inhibition of fish reproduction or maturation results in increased weight of the treated fish.

19. The method of claim 17, wherein fish is selected from the group consisting of: tilapia, carp, salmon, bass, catfish and mullet.

20. The method of claim 17, wherein the composition is administered to fish by a route selected from the group consisting of: parenteral, oral and administration by immersion.

* * * * *